(12) United States Patent
Kamada et al.

(10) Patent No.: US 6,410,020 B1
(45) Date of Patent: *Jun. 25, 2002

(54) MONOCLONAL ANTIBODY REACTIVE TO HUMAN CETP AND ASSAY METHOD FOR HUMAN CETP

(75) Inventors: Masafumi Kamada, Kanagawa; Hiroshi Okamoto, Osaka; Takuya Tamatani, Kanagawa, all of (JP)

(73) Assignee: Japan Tobacco, Inc., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/615,404

(22) Filed: Jul. 12, 2000

Related U.S. Application Data

(62) Division of application No. 08/945,646, filed as application No. PCT/JP96/01191 on May 1, 1996, now Pat. No. 6,140,474.

(30) Foreign Application Priority Data

May 2, 1995 (JP) .............................................. 7-134836

(51) Int. Cl.[7] ........................ C07K 16/00; A61K 39/395
(52) U.S. Cl. ................................ 424/133.1; 530/387.3; 530/388.1; 530/388.25; 530/391.3; 530/391.1; 424/130.1; 424/134.1; 424/141.1; 424/142.1; 424/178.1; 435/7.92; 435/810
(58) Field of Search ..................... 530/388.85, 391.3; 424/133.1, 130.1; 435/810, 7.92

(56) References Cited

U.S. PATENT DOCUMENTS 5,279,540 A    1/1994  Davidson
5,530,101 A    6/1996  Queen
6,140,474 A  * 10/2000 Kamada et al.

OTHER PUBLICATIONS

Bendig et al, Humanization of Rodent Monoclonal Antibodies by CDR Grafting, 1995, Methods: A companion to Mehtods in Enzymology 8: 83–93.*
Swenson et al, Mechanism of Cholesteryl Ester Transfer Protein Inhibition by a Neutralizing Monoclonal Antiobdy and Mapping of the Monoclonal Antibody Epitope, 1989, J. Biol. Chem. 264(24): 14318–26.*
R. W. Clark et al., *J. Lipid Res.*, vol. 36, pp. 876–889 (1995).
Whitlock, Mary E. et al., *J. Clin. Invest.*, vol. 84, (Jul. 1989), 129–137.
Marcel, Yves L. et al., *J. Clin. Invest.*, vol. 85, (Jan. 1990), 10–17.
Mezdour et al. *Clin. Chem.* 40:593, 1994.
Wang, et al. *J. Biol. Chem.*, 267:17487, 1992.
Hesler et al., *J. Biol. Chem.* 263:5020, 1988.
Agellon et al. *J. Biol. Chem.* 266:10796, 1991.
Swenson et al. *J. Biol. Chem.* 264:14318, 1989.

* cited by examiner

Primary Examiner—Christina Y. Chan
Assistant Examiner—Phuong N. Huynh
(74) Attorney, Agent, or Firm—Birch, Stewart, Kolasch & Birch, LLP

(57) ABSTRACT

Monoclonal antibodies which have binding specificity to human CETP(CETP inhibition activity) and which are useful as reagents for purification or quantification of human CETP, and as pharmaceuticals to prevent and/or treat hyperlipidemia or arteriosclerosis are provided. Furthermore, purification and quantification methods of human CETP by using the monoclonal antibodies are also provided.

14 Claims, 25 Drawing Sheets

Effect of antibody administration on HDL cholesterol amount in plasma of human CETP-expressing Tg mouse

MONOCLONAL ANTIBODY REACTIVE TO HUMAN CETP AND ASSAY METHOD FOR HUMAN CETP

This application is a divisional of application Ser. No. 08/945,646, filed on Oct. 31, 1997, now U.S. Pat. No. 6,140,474. application Ser. No. 08/945,646 is the national phase of PCT International Application No. PCT/JP96/01191/ filed on May 1, 1996 under 35 U.S.C. §371. The entire contents of each of the above-identified applications are hereby incorporated by reference.

FIELD OF THE INVENTION

The present invention relates to hybridomas producing a monoclonal antibody reactive to human cholesterol ester transfer protein(CETP), a monoclonal antibody and its fragment reactive to human CETP, an immobilized monoclonal antibody and immobilized antibody fragment, a labeled monoclonal antibody and labeled antibody fragment, a kit for detection, assay, separation or purification of human CETP, a method for detection, assay, separation and purification of human CETP and a pharmaceutical composition containing said monoclonal antibody or said antibody fragment.

BACKGROUND OF THE INVENTION

There are three types of cholesterol, free type, long chain fatty acid type and ester type, in all the tissues and blood plasma in organisms. The former two play important roles in the composition of cell membranes. The latter is physiologically inactive and exists mainly in a storage form. Cholesterols in a body are derived from ingestion in the small intestine or from biosynthesis in various tissues, especially in the liver. Most cholesterols are derived from biosynthesis in the liver.

Free cholesterol biosynthesized and secreted from the liver is incorporated in very low density lipoprotein(VLDL). Then, by the actions of lipoprotein lipase(LPL) and hepatic triglyceride lipase(HTGL), it is metabolized to low density lipoprotein (LDL) through intermediate density lipoprotein (IDL). By the incorporation of LDL into LDL receptors of peripheral cells, free cholesterol is supplied to cells.

There is a pathway from the peripheral cells to the liver called the cholesterol reverse transfer system, which goes in reverse of the way from liver to peripheral cells as mentioned above. Surplus free cholesterol supplied in the peripheral cells from the liver is drawn by high density lipoprotein(HDL) in blood. Then, by the action of lecithin cholesterol acyl transferase(LCAT), it is converted to cholesterol ester and is stored in high density lipoprotein(HDL) in blood. By the action of cholesterol ester transfer protein (CETP), the cholesterol ester stored in HDL is transferred to VLDL, IDL or LDL in blood. By the incorporation of VLDL, IDL or LDL cholesterol ester received through LDL receptors in the liver, cholesterol is indirectly transferred to the liver.

Recently, the reverse cholesterol transfer system has drawn much attention as a mechanism for preventing the peripheral cells from accumulating cholesterol and thereby preventing atherosclerosis. In fact, as for HDL which plays an important role in the reverse cholesterol transfer system, many epidemiological surveys show that decrease of cholesterol ester in blood HDL is one of the risk factors of coronary artery disorders. It is now well recognized that HDL is a lipoprotein having anti-arteriosclerosis action.

In addition to the importance of blood HDL, it became recognized that CETP is also important because it mediates transfer of cholesterol ester in HDL into blood LDL. Therefore, it became an urgent matter to elucidate the relationship between CETP and various diseases such as CETP deficiency, hyperlipidemia, hyperalphalipoproteinemia, hypercholesterolemia, hypolipidemia, arteriosclerosis, diabetes and nephrotic syndrome.

For instance, it is experimentally demonstrated that several times higher CETP are secreted in blood of the patients with hyperlipidemia compared to those of healthy volunteers. The following findings have been made in relation to arteriosclerosis. When CETP activity is low, arteriosclerosis is not easily induced and the level of HDL cholesterol is high. In contrast, when CETP activity is high, arteriosclerosis is easily induced and the level of HDL cholesterol is low. Such relationships have been experimentally demonstrated(Current Therapy, vol. 7, 9:36–45(1989)).

In order to elucidate the relationship between various diseases and CETP, assay methods for CETP in body fluids such as blood plasma from a healthy person or patient having the above various diseases, especially immunoassay methods such as radio-immunoassay(RIA) by using a monoclonal antibody against CETP(anti-CETP monoclonal antibody), or enzyme-immunoassay(EIA, ELISA) are being developed together with an anti-CETP monoclonal antibody used for the assay methods.

As to EIA(ELISA) assay with the anti-CETP monoclonal antibody, there are the examples by Imai et al.(Japanese Unexamined Patent publication No.HEI6-169793), Nakano, et al.,(Arteriosclerosis, vol. 19, 11:951, No. 22, (1991)), Takahama, et al.(Arteriosclerosis, vol. 20, 10:837, No. 135, (1992)), Sato, et al.(Arteriosclerosis, vol. 20, 10:836, No. 134, (1992)), H. Mezdur, et al.(Clinical Chemistry, vol. 40, 4:593–597(1994)). Clark et al.(Journal of Lipid Research, vol. 36,:876–889(1995)) reported the sandwich ELISA method by using two kinds of anti-CETP monoclonal antibodies or their Fab' fragments.

However, these assay methods require complicated handling. Before assay, a plasma sample has to be heat-treated at 95–100° C. and/or pre-treated with surface active agents (surfactants, detergent) such as TWEEN 20 and TRITON X-100. Since heat treatment of a plasma sample causes denaturation of CETP in the sample, the assay result tells only the amount of denatured CETP. Therefore, it is impossible to assay intact CETP in a plasma sample accurately.

Also, R. Clark et al.(FASEB Journal, vol. 8, 7:A1343 No. 495(1994)), Takahashi et al.(Arteriosclerosis, vol. 20, 10:837 No. 136(1992) and ibid. vol. 21, 3:209 No. 97(1993)), Kanamitu et al.(ibid. vol. 21, 3:209 No. 98(1993)) and Waki et al.(ibid. vol. 22, 5:441 No. 194 (1994)) reported assay results on CETP in plasma samples by ELISA, however, they did not describe in detail their preparation methods, properties of anti-CETP antibodies and specific assay procedures.

Regarding RIA assay methods with anti-CETP monoclonal antibody, Fukazawa et al.(Study on lipid biochemistry, vol. 34:163–166(1992)), Y. Marcel et al.(J. Clin. Invest., vol. 85:10–17(1990) and Adv. Exp. Med. Biol., vol. 243:225–230(1988)), Fukazawa et al.(J. Biochem., vol. 111:696–698(1992)), J.Koizumi et al. (Atherosclerosis, 90:189–196(1991), M. Brown et al.(Nature, vol. 342:448–451(1989)) and V. Dangremont et al.(Clinica Chimica Acta, vol. 231:147–160(1994)) published reports thereon.

However, these RIA methods also had the same defects as the EIA(ELISA) method had. The defects were complexity of handling (the methods required pre-treatment of a plasma sample with a detergent) and/or insufficient sensitivity for detection.

As described above, many researchers tried to establish an assay method for CETP. However, there is no report of a convenient and sensitive system which needs no pretreatment of a sample and which determines conveniently the amount of intact CETP with high sensitivity.

To elucidate the relationship between the diseases (such as arteriosclerosis, hyperlipidemia hyperalphalipoproteinmia and hypercholesterolemia) and CETP that plays an important role in the cholesterol reverse transfer system which may be highly related to the onset of the diseases, there is a strong reason for developing a simple and sensitive assay method that can be widely applied to clinical purposes to assay intact CETP in a body fluid including blood plasma from healthy persons or any patients, and for developing a monoclonal antibody useful for said assay method. However, these have not yet been established. The present invention provides an assay method widely applicable for clinical purposes and an anti-human CETP monoclonal antibody which is very useful not only for said assay method but also as a reagent for separation and purification of CETP and as a pharmaceutical product.

SUMMARY OF THE INVENTION

The inventors of the present invention extensively investigated assay methods for CETP in a human body fluid that can be widely applicable for clinical purposes and monoclonal antibodies against human CETP used for said assay methods. By using biologically active purified human CETP as an immunogen, the inventors succeeded in preparing three anti-human CETP monoclonal antibodies which respectively have different high binding specificity(CETP inhibitory activity) to human CETP, especially intact CETP in the human body fluid.

Furthermore, as the three anti-human CETP monoclonal antibodies have high binding specificity(CETP inhibitory activity) to human CETP, especially intact CETP in a human body fluid, the inventors have found that, for assaying intact CETP in the human body fluid(blood plasma etc.), the immunoassay using the anti-human CETP monoclonal antibodies of the present invention can provide a simple and sensitive assay method which has not been previously established.

Particularly, as the three anti-human CETP monoclonal antibodies have high but different binding specificity(CETP inhibitory activity) to human CETP(especially to intact CETP in the human body fluid), by using a combination of any of the two of the three monoclonal antibodies for sandwich ELISA, the inventors were succeeded in developing a simpler and more sensitive assay method widely applicable for clinical purposes.

As the anti-human CETP monoclonal antibodies have high binding specificity(CETP inhibitory activity) to human CETP(especially to intact CETP in the human body fluid), it is possible to assay human CETP simply and sensitively without any pre-treatment such as heat or detergent treatment of a plasma sample using the monoclonal antibodies of the invention.

In addition, as the anti-human CETP monoclonal antibodies of the invention have high CETP inhibitory activity, they are useful as pharmaceuticals for treatment or prevention of various diseases caused by abnormal dynamics of CETP such as arteriosclerosis, hyperlipidemia, high blood HDL and hypercholesterolemia.

The first aspect of the present invention is a monoclonal antibody having at least the following characteristics:
(a) reactive to plasma CETP(Cholesterol Ester Transfer Protein) of a healthy human, hyperlipidemia patients, LCAT(Lecithin Cholesterol Acyl Transferase) deficiency patients or hyper HDL (high density lipoprotein) patients.
(b) not reactive to rabbit CETP at a concentration of 3 $\mu$g/ml or below.
(c) not specifically reactive to denatured human CETP.

A second aspect of the present invention is the hybridomas which produce monoclonal antibodies reactive to human CETP, and more specifically, hybridomas #72-1 and #86-2 identified by the Accession Number FERM BP-4944 and FERM BP-4945 respectively.

A third aspect of the present invention is the monoclonal antibodies reactive to human CETP, and more specifically, monoclonal antibodies #72-1 and #86-2, which are derived respectively from the hybridomas #72-1 and #86-2 identified by the Accession Number FERM BP-4944 and FERM BP-4945 respectively.

A fourth aspect of the present invention is a recombinant chimeric monoclonal antibody reactive to human CETP, comprising a variable region derived from that of the above-mentioned monoclonal antibody and a constant region derived from that of human immunoglobulin.

A fifth aspect of the present invention is a recombinant humanized monoclonal antibody reactive to human CETP, in which a part of or the whole of the complementarity determining regions of the hypervariable region is derived from that of the above-mentioned monoclonal antibody, the framework regions of the hypervariable region are derived from that of human immunoglobulin, and the constant region is derived from that of human immunoglobulin.

A sixth aspect of the present invention is an antibody fragment termed F(ab')$_2$ or Fab' derived from the above-mentioned monoclonal antibody, the above-mentioned recombinant chimeric monoclonal antibody, or the above-mentioned recombinant humanized monoclonal antibody.

The seventh aspect of the present invention is an immobilized monoclonal antibody and an immobilized antibody fragment. The immobilized monoclonal antibody is prepared by immobilizing the monoclonal antibody, the recombinant chimeric monoclonal antibody or the recombinant humanized monoclonal antibody on an insoluble carrier. The immobilized antibody fragment is prepared by immobilizing the above mentioned antibody fragment F(ab')$_2$ or Fab' on an insoluble carrier.

More specifically, the immobilized monoclonal antibody or the immobilized antibody fragment is that which has been immobilized on a plate, a test tube, a tube, beads, a ball, a filter, a membrane or an insoluble carrier used for affinity column chromatography.

The eighth aspect of the present invention is a labeled monoclonal antibody and a labeled antibody fragment. The labeled monoclonal antibody is prepared by labeling the monoclonal antibody, the recombinant chimeric monoclonal antibody or the recombinant humanized monoclonal antibody with a substance capable of providing detectable signals independently or by reaction with another substance. The labeled antibody fragment is prepared by labeling the antibody fragment, F(ab')$_2$ or Fab', with a substance capable of providing detectable signals independently or by reaction with another substance.

The monoclonal antibody or antibody fragment can be labeled with an enzyme, a fluorescent material, a chemical luminous material, biotin, avidin or radioisotopes.

A ninth aspect of the present invention is a kit for assay or detection of human CETP comprising at least the monoclonal antibody, the recombinant chimeric monoclonal antibody or recombinant humanized monoclonal antibody, the above-mentioned antibody fragment F(ab')$_2$ or Fab', the immobilized monoclonal antibody or immobilized antibody fragment, or the labeled monoclonal antibody or the labeled antibody fragment.

Specifically, the invention involves a kit for assay or detection of human CETP comprising the immobilized monoclonal antibody or the immobilized antibody fragment and the labeled monoclonal antibody or the labeled antibody fragment.

Ae tenth aspect of the present invention is a method for assay and detection of human CETP by immunoassay characterized by using at least the monoclonal antibody, the recombinant chimeric monoclonal antibody or the recombinant humanized monoclonal antibody, the antibody fragment F(ab')$_2$ or Fab', the immobilized monoclonal antibody or the immobilized antibody fragment, or the labeled monoclonal antibody or the labeled antibody fragment.

The first specific aspect is a method for assay or detection of human CETP by immunoassay comprising at least the following steps:
  (a) reacting a sample with the above-mentioned immobilized monoclonal antibody or the immobilized antibody fragment; and
  (b) reacting the labeled monoclonal antibody or the labeled antibody fragment with an antigen-antibody complex which is formed by binding human CETP in a sample with the immobilized monoclonal antibody or the immobilized antibody fragment.

The second specific aspect is a method for assay or detection of human CETP by immunoassay comprising at least the following steps:
  (a) reacting a sample with the above-mentioned labeled monoclonal antibody or the labeled antibody fragment; and
  (b) reacting the above-mentioned immobilized monoclonal antibody or the immobilized antibody fragment with an antigen-antibody complex which is formed by binding human CETP in a sample with the labeled monoclonal antibody or the labeled antibody fragment.

The third specific aspect is a method for assay or detection of human CETP by immunoassay comprising at least the following step:
  (a) reacting a mixture comprising the immobilized monoclonal antibody or the immobilized antibody fragment, the labeled monoclonal antibody or the labeled antibody fragment and a sample.

The fourth specific aspect is a method for assay or detection of human CETP by immunoassay comprising at least the following step:
  (a) reacting a sample and a human CETP standard labeled with a labeling substance capable of providing detectable signals independently or by reaction with another substance with the above-mentioned immobilized monoclonal antibody or the immobilized antibody fragment.

The fifth specific aspect is a method for assay or detection of human CETP by immunoassay comprising at least the following step (a) or following steps (b) and (c):
  (a) reacting the above-mentioned monoclonal antibody or antibody fragment with a mixture of a sample and a labeled human CETP standard which is prepared by labeling with a substance capable of providing detectable signals independently or by reacting with other substances;
  (b) reacting the above-mentioned monoclonal antibody or the antibody fragment with a sample;
  (c) followed by the step (b), reacting the labeled human CETP standard with the reaction mixture of step (b), in which the labeled human CETP standard is prepared by labeling with a substance capable of providing a detectable signal independently or by reacting with other substances.

More specifically, a method for assay or detection of human CETP by immunoassay comprising at least the following steps (a) and (d), or steps (b) to (d):
  (a) reacting the monoclonal antibody or the antibody fragment of the present invention with a mixture of a sample and a labeled human CETP standard that is prepared by labeling with a substance capable of providing a detectable signal independently or by reacting with other substances;
  (b) reacting the monoclonal antibody or the antibody fragment of the present invention with a sample;
  (c) followed by step (b), reacting a labeled human CETP standard with the reaction mixture of step (b), in which the labeled human CETP standard is prepared by labeling with a substance capable of providing a detectable signal independently or by reaction with other substances;
  (d) reacting an antiserum derived from a mammal reactive with the monoclonal antibody or the antibody fragment with an antigen-antibody complex which is formed by binding human CETP in the sample or the labeled human CETP standard with the monoclonal antibody or the antibody fragment.

An eleventh aspect of the present invention is a kit for separation or purification of human CETP comprising an immobilized monoclonal antibody or an immobilized antibody fragment.

A twelfth aspect of the present invention is a method for separation or purification of human CETP by affinity chromatography using an immobilized monoclonal antibody or an immobilized antibody fragment. More specifically, it is a purification method for human CETP using column chromatography.

A thirteenth aspect of the present invention is a mouse expressing a DNA encoding human CETP which constantly secretes human CETP the in blood without extrinsic or artificial induction.

A fourteenth aspect of the present invention is a pharmaceutical composition comprising any one of monoclonal antibodies, a recombinant chimeric monoclonal antibody, a recombinant humanized monoclonal antibody or an antibody fragment (F(ab')$_2$ or Fab'), and a pharmaceutically acceptable carrier. More specifically, it is a pharmaceutical composition for treating and/or preventing hyperlipidemia or arteriosclerosis.

Figure 1:
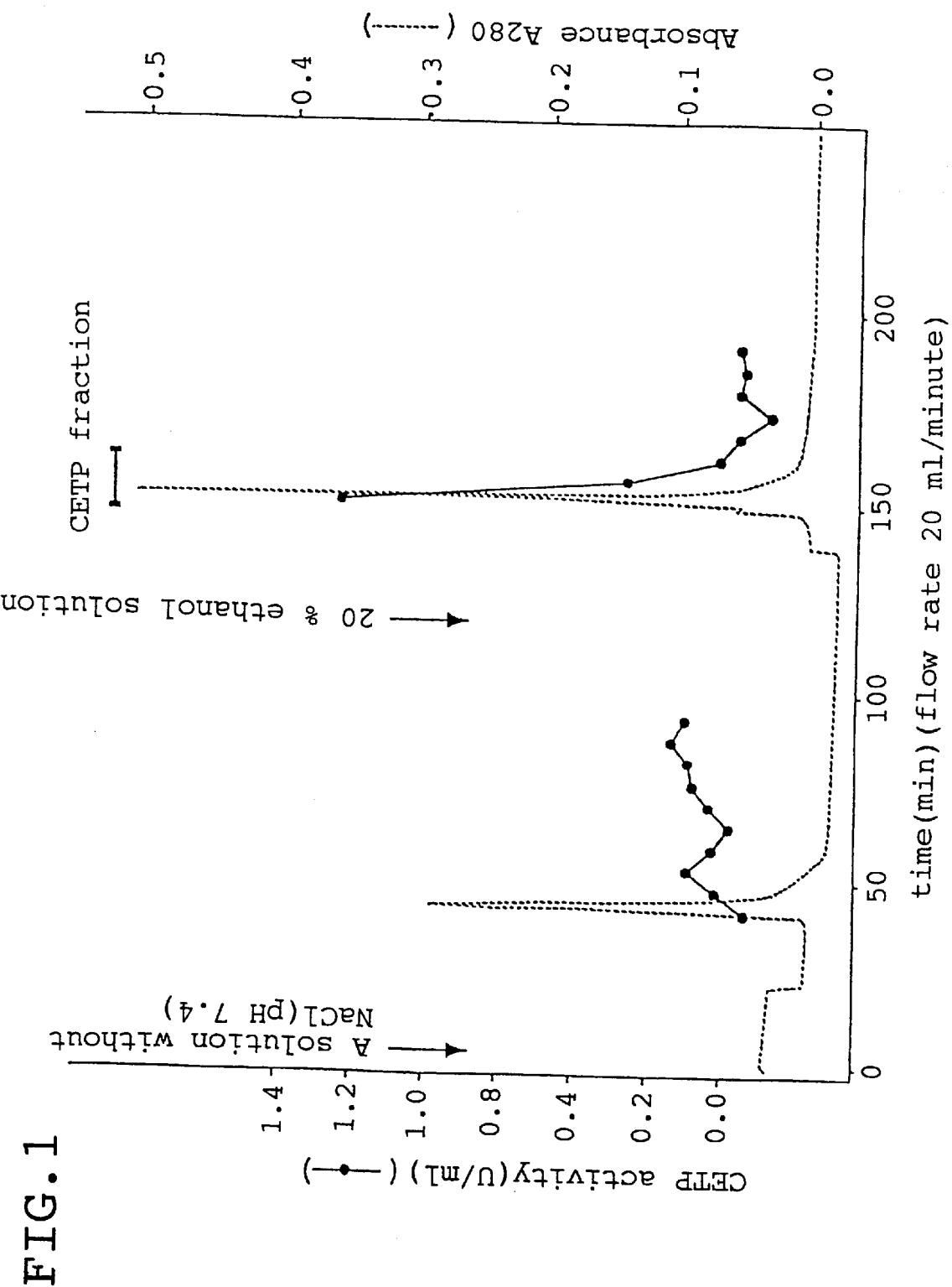
FIG. 1 shows a chromatogram of human CETP by PHENYL SEPHAROSE column chromatography.

By clarifying the meaning of the terms used here, the present inventions are explained in detail.

A "monoclonal antibody" of the present invention means a monoclonal antibody reactive to human CETP and more specifically, a monoclonal antibody having at least the following characteristics (a), (b) and (c).

(a) Reactive to plasma CETP(Cholesterol Ester Transfer Protein) of a healthy human, hyperlipidemia patients, LCAT(Lecithin Cholesterol Acyl Transferase) deficiency patients or hyper HDL(high density lipoprotein) patients.

(b) Not reactive to rabbit CETP at a concentration of 3 $\mu$g/ml or below.

(c) Not specifically reactive to denatured human CETP.

In addition, the monoclonal antibody of the present invention has a characteristic that it is reactive to intact CETP in a human body fluid.

"Denatured human CETP" mentioned here means human CETP of which higher-order structure(conformation) of the protein has been destroyed by treatment such as heat treatment or treatment with detergent (TWEEN 20, TRITON X-100 etc.), or that which is biologically inactive.

More specifically, "monoclonal antibody" of the present invention means the monoclonal antibodies #72-1 and #86-2 derived from the hybridomas #72-1 and #86-2 identified by Accession Number FERM BP-4944 and FERM BP-4945 respectively, and the monoclonal antibody #176-1 produced from the hybridoma #176-1 prepared in the example described below.

Furthermore, it includes a recombinant chimeric monoclonal antibody and a recombinant humanized monoclonal antibody derived from the monoclonal antibody, which can be prepared by genetic recombination, and also includes a human monoclonal antibody.

The monoclonal antibodies of the present invention(for example, #72-1, #86-2 and #176-1) can be prepared by conventional preparation methods established for monoclonal antibodies. For instance, they can be produced from hybridomas prepared by cell fusion. That is, by immunizing mammals with antigen, antibody producing cells can be obtained. Hybridoma cells are prepared from the antibody producing cells with myeloma cells which do not have an ability to produce autoantibody. After cloning the hybridoma, clones which produce monoclonal antibodies showing specific affinity for the antigen used for immunization of the mammals are selected and then, the monoclonal antibodies of the present invention are produced from the hybridomas.

Specifically, non-denatured, intact, and biologically active purified human CETP is used as an antigen. A mammal (including transgenic animals such as a genetically engineered mouse which produces a human antibody), more specifically, mouse, rat, hamster or guinea pig, is immunized with said antigen by injecting the antigen one to several times subcutaneously, intramuscularly, intravenously, into the foot pad or intraperitoneally.

In general, immunization is performed one to four times every one to fourteen days from the initial immunization. Antibody producing cells are obtained from the immunized mammal approximately one to five days after the final immunization.

The hybridoma which secretes monoclonal antibody can be prepared according to the method by Köhler, and Milstein et al.(Nature, vol. 256:495–497(1975)) or according to a modified method similar to the original method. Hybridomas are prepared by cell fusion of antibody producing cells and myeloma cells. The antibody producing cells are obtained from the spleen, the lymph node, the bone marrow or the tonsil, the preferably the spleen, of mammals, immunized according to the above-mentioned procedures. The myeloma cells incapable of producing autoantibody are derived from mammals preferably from a mouse, rat, guinea pig, hamster, rabbit or human, more preferably from a mouse, rat or human.

As myeloma cells to be used for cell fusion, for example, mouse derived myeloma P3/X63-AG8.653(653), P3/NS1/1-Ag4-1(NS-1), P3/X63-Ag8.U1(P3U1), SP2/0-Ag14(Sp2/O, Sp2), PAI, F0 or BW5147, rat derived myeloma 210RCY3-Ag.2.3., human derived myeloma U-266AR1, GM1500-6TG-A1-2, UC729-6, CEM-AGR, D1R11 or CEM-T15 and so forth can be used.

Screening of hybridomas can be performed by culturing the hybridomas on a microtiter plate as an example, and then, measuring reactivity to purified human CETP used for the immunization of the culture supernatant of wells which showed cell-proliferation. The screening assay can be performed by RIA or by enzyme immunoassay such as ELISA.

Preparation of a monoclonal antibody from the hybridoma is performed by culturing the hybridoma in vitro or by placing the hybridoma in vivo in ascites of a mouse, rat, guinea pig, hamster or rabbit, preferably in ascites of a mouse or rat, but more preferably in ascites of a mouse, and then, by isolating the monoclonal antibody from the culture supernatant or from the ascites of mammals.

In a case of culturing a hybridoma in vitro, depending on the characteristics of cells, purpose of study, culturing method and so forth any known nutrient medium or any kind of nutrient medium modified from known basic media can be used as long as the medium is usable to proliferate, maintain and keep the hybridoma and to produce monoclonal antibody in culture supernatant.

As a basic medium, for example, low calcium medium such as HamF12 medium, MCDB153 medium and low calcium MEM medium and high calcium medium such as MCDB104 medium, MEM medium, D-MEM medium, RPMI1640 medium, ASF104 medium or RD medium can be used. Depending on the purpose of culture, said basic medium may contain, for example, serum, hormones, cytokines and/or various inorganic or organic substances.

Isolation and purification of the monoclonal antibody from the above-mentioned culture supernatant or ascites can be performed by applying saturated ammonium sulfate precipitation, euglobulin precipitation, the caproic acid method, the caprylic acid method, ion exchange chromatography(DEAE, DE52 or the like), or affinity column chromatography such as anti-immunoglobulin column chromatography and protein A column chromatography, and so forth.

"Recombinant chimeric monoclonal antibody" of the present invention means a genetically engineered monoclonal antibody, specifically chimeric monoclonal antibody such as recombinant mouse/human chimeric monoclonal antibody comprising a variable region derived from that of the above-mentioned monoclonal antibody such as the monoclonal antibody #72-1, #86-2 or #176-1 and a constant region derived from that of human immunoglobulin. The constant regions derived from human immunoglobulins have different unique amino acid sequences based on their isotype such as IgG, IgM, IgA, IgD and IgE. The constant region of human immunoglobulin of any isotype can be provided as the constant region of the recombinant chimeric monoclonal antibody of the present invention. The constant region of human IgG is preferable.

A recombinant mouse/human chimeric monoclonal antibody derived from the monoclonal antibody #72-1, #86-2 or #176-1 included in the monoclonal antibodies of the present invention can be prepared as follows, however, it is not limited to the following preparation method.

The recombinant chimeric monoclonal antibody can be prepared, for example, by referring to Experimental Medicine(special edition) vol. 1–6, No. 10, 1988 and Japanese patent publication No. HEI 3-73280. Downstream of the active VH gene(rearranged VDJ gene encoding the variable region of the H chain), the CH gene(C gene encoding the constant region of the H chain) is operably linked thereto, and downstream of the active VL gene (rearranged VJ gene encoding the variable region of the L chain), the CL gene(C gene encoding the constant region of the L chain) is operably linked thereto. These genes are inserted in the same vector or different expression vectors. The VH gene used here is obtained from DNA encoding the monoclonal antibody #72-1, #86-2 or #176-1 isolated from the hybridoma #72-1, #86-2 or #176-1 of the present invention. The CH gene and the CL gene are obtained from DNA encoding human immunoglobulin. The VL gene is obtained from DNA encoding the monoclonal antibody #72-1, #86-2 or #176-1 isolated from the hybridoma #72-1, #86-2 or #176-1 of the present invention. Host cells are transformed with the vector(s). The recombinant mouse/human chimeric monoclonal antibody of the present invention can be prepared by culturing said transformed cells. As a host cell, prokaryotic cells (e.g. *E. coli*) or eukaryotic cells (e.g. CHO cells) can be used.

Briefly, after DNA is extracted from the hybridomas #72-1, #86-2 or #176-1 by a conventional method, the DNA is digested with appropriate restriction enzymes such as EcoRI and HindIII. Then, Southern blotting is performed by electro-phoresis (for example, with 0.7% agarose gel). After the electrophoresis, the gel is stained(for example, with ethidium bromide). After taking a photograph of the gel, the location of the marker is marked and the gel is washed twice; then, the gel is immersed in 0.25 M HCl solution for 15 minutes. Then the gel is immersed in 0.4 N NaOH for 10 minutes with gentle shaking. By a conventional method, the gel is transferred on a filter and after 4 hours left standing, the filter is recovered and is washed twice with 2×SSC. After drying the filter completely, the filter is baked at 75° C. for 3 hours. After the baking, the filter is put in 0.1×SSC/0.1% SDS solution and is treated for 30 minutes at 65° C. The filter is immersed in 3×SSC/0.1% SDS solution. Then the filter is put in a vinyl bag with the pre-hybridization solution and left standing for 3 to 4 hours at 65° C.

Then, $^{32}$p labeled DNA probe and the hybridization solution are added, and the mixture is reacted for approximately 12 hours at 65° C. After hybridization, the filter is washed at an appropriate salt concentration, reaction temperature and time period(as an example, with 2×SSC-0.1% SDS solution, at room temperature for 10 minutes). the filter is then put in a vinyl bag and a small amount of 2×SSC is added, and the bag is closed tightly and autoradiography is performed.

By the above-mentioned Southern blotting, the rearranged VDJ gene and VJ gene, which respectively encode, the H chain and the L chain of the monoclonal antibody #72-1, #86-2 or #176-1, are identified. The region including the identified DNA fragment is fractionated by sucrose density gradient centrifugation and incorporated into a phage vector (such as Charon 4A, Charon 28, λEMBL3 and λEMBL4). By transforming *E. coli*(such as LE392 and NM539) with the phage vector, a genome library is established. By plaque hybridization with an appropriate probe(such as H chain J gene and L chain(κ) J gene) according to the Benton-Davis method(Science, vol. 196, p.180–182, 1977), positive clones containing the rearranged VDJ gene or VJ gene respectively are obtained from the genome library. A restriction enzyme map of the obtained clones is made, the nucleotide sequence is determined and the existence of the rearranged VH(VDJ) gene or VL(VJ) gene is confirmed.

On the other hand, the human CH gene and human CL gene used for chimerization are isolated separately. For instance, to prepare a chimeric antibody with human IgG1, a Cγ1 gene(CH gene) and a Cκ gene(CL gene) are isolated. These genes can be isolated from a human genome library by using a mouse Cγ1 gene(corresponds to the human Cγ1 gene) and a mouse Cκ gene(corresponds to the human Cκ gene) as probes because the nucleotide sequences of the mouse immunoglobulin gene and the human immunoglobulin gene are highly homologous.

Briefly, as an example, a DNA fragment containing the human Cκ gene and the enhancer region can be isolated from human HaeIII-AluI genome library in the vector, Charon 4A (Cell, vol. 15:1157–1174(1978)) using a HindIII-BamHI fragment(3 kb) obtained from the clone Ig146(Proc. Natl. Acad. Sci. USA, vol. 75:4709–4713(1978) and an EcoRI fragment(6.8 kb) obtained from the clone MEP10 (Proc. Natl. Acad. Sci. USA, vol. 78:474–478(1981)) as probes. The human Cγ1 gene can be isolated, for example, by digesting DNA from the human fetal liver cells with HindIII, fractionating by agarose gel electrophoresis, inserting the 5.9 kb band into λ788 and then isolating with the above-mentioned probes.

Using the isolated mouse VH gene, mouse VL gene, human CH gene and human CL gene, and considering the promoter region and the enhancer region, the human CH gene is placed downstream of the mouse VH gene and the human CL gene is placed downstream of the mouse VL gene in a expression vector such as pSV2gpt and pSV2neo by using an appropriate restriction enzyme and DNA ligase. In this case, the mouse VH gene/human CH gene and the mouse VL gene/human CL gene can be placed in one expression vector or in different expression vectors.

The chimeric gene inserted in the expressed vector(s) is introduced into myeloma cells which do not produce antibodies such as P3X63-Ag8-653 cells and SP210 cells by the protoplast fusion method, DEAE-dextran method, calcium phosphate method or electroporation. The transformed cells are selected by culturing them in culture medium containing a drug which corresponds to the drug resistant gene inserted in the expression vector(s), and thus chimeric monoclonal antibody producing cells can be obtained.

The chimeric monoclonal antibody can be obtained from the culture supernatant of the selected antibody producing cells. .

"A recombinant humanized monoclonal antibody" of the present invention means genetically engineered monoclonal antibody. Specifically, it means that a part of or the whole of the complementarity determining regions of the hypervariable region is derived from that of the above-mentioned monoclonal antibody(monoclonal antibody #72-1, #86-2 or #176-1 as examples), the framework regions of the hypervariable region are derived from that of human immunoglobulin, and the constant region is derived from that of human immunoglobulin.

The complementarity determining region(s) in the hypervariable region means three regions(CDR1, CDR2, CDR3) which exist in the hypervariable region of the variable region of the antibody and complementarily bind directly with the antigen. The framework region(s) in the hypervariable region means the four regions(FR1, FR2, FR3, FR4) which are located between (before and after) the three complementarity determining regions, and are relatively well conserved.

In other words, "recombinant humanized monoclonal antibody" means monoclonal antibody in which all of the parts except for a part of or the whole of the complementarity determining regions of the hypervariable region of the monoclonal antibodies of the present invention are replaced with corresponding region(s) of human immunoglobulin.

The constant region derived from human immunoglobulin has a unique amino acid sequence according to the isotype such as IgG, IgM, IgA, IgD and IgE. The constant region of the recombinant humanized monoclonal antibody of the present invention may be the constant region of any isotype of human immunoglobulin, but preferably it is the constant region of human IgG. The framework region(s) in the hypervariable region derived from human immunoglobulin is not limited to those from one isotype.

The recombinant humanized monoclonal antibody derived from the monoclonal antibody #72-1, #86-2 or #176-1 included in the monoclonal antibodies of the present invention can be prepared, for example, by the following steps but not limited to the following.

For instance, the recombinant humanized monoclonal antibody can be prepared by genetic engineering techniques according to Japanese Patent Unexamined Publication Number HEI4-506458 and Japanese Patent Unexamined Publication Number SYOU62-296890. From the hybridoma #72-1, #86-2 or #176-1, at least one mouse H chain CDR gene and at least one mouse L chain CDR gene which correspond to the mouse H chain CDR genes are isolated. From the human immunoglobulin gene, the human H chain gene which encodes the whole region except the human H chain CDR(corresponds to mouse H chain CDR), and human L chain gene which encodes the whole region except the human L chain CDR(corresponds to the mouse L chain CDR) are isolated. The isolated mouse H chain CDR genes and the human H chain gene are operably linked and are introduced into an appropriate expression vector, and, similarly, the mouse L chain CDR genes and the human L chain gene are operably linked and are introduced into another appropriate expression vector. Or otherwise, it is possible to introduce the mouse H chain CDR genes/human H chain gene and the mouse L chain CDR genes/human L chain gene into one expression vector. By transforming the host cells with the obtained expression vector(s), transformed cells which produce the humanized monoclonal antibody can be obtained. By culturing said transformed cells, the humanized monoclonal antibody can be obtained from the culture supernatant.

As host cells, both prokaryotic cells such as *E. Coli* and eukaryotic cells such as CHO(Chinese hamster ovarian) cells may be used.

The term "human antibody" in the present invention means that the immunoglobulin of which entire regions including both the constant and variable regions of the heavy chains and the light chains are derived from genes encoding human immunoglobulin.

The human antibody is produced according to a common method as follows. For example, the human immunoglobulin genes are integrated into a gene locus of animals such as mice (except a human) to obtain transgenic animals producing human antibody. Then, the transgenic animal is immunized using any antigen. Thus, polyclonal and/or monoclonal antibodies are obtained in the same manner described above. For instance, such transgenic mice producing human antibodies are produced by using the method disclosed in several references: Nature Genetics, 7:13–21(1994), Japanese patent Unexamined No. HEI4-504365, International Patent Publication No. WO94/25585 NIKKEI Science, June: 40–50(1995), Nature, 368:856–859(1994), and national publication of the translated version No. 1995-500233.

"F(ab')" or "Fab'" of the present invention means antibody fragments produced by treating immunoglobulin (monoclonal antibody) with a protease such as pepsin or papain. These terms refer to the antibody fragment(s) digested at positions before and after the disulfide bonds between the two H chains in the hinge region. For example, when IgG1 is treated with papain, it is cleaved upstream from the disulfide bond between the two H chains in the hinge region to produce two identical fragments, which comprise a L chain comprising VL(L chain variable region) and CL(L chain constant region), and a H chain fragment comprising VH(H chain variable region) and CHγ1(γ1 region of the constant region of H chain) which are bound at the C terminal region by a disulfide bond. Each of the two identical fragments is called Fab'. When treated with pepsin, IgG1 is cleaved downstream from the disulfide bond between the two H chains at the hinge region to make one antibody fragment which is a little larger than a fragment consisting of two Fab' by connecting those at the hinge region. This antibody fragment is called F(ab')$_2$.

"Antiserum derived from a mammal" of the present invention means a serum containing an antibody reactive to the monoclonal antibody of the present invention or its antibody fragment. The serum is prepared by immunizing a mouse, rat, guinea pig, rabbit, goat, pig or bovine, but preferably a rat, guinea pig, rabbit or goat, with the monoclonal antibody or the antibody fragment of the present invention according to the procedures described above for preparing the above mentioned monoclonal antibody. More, specifically, it is an antiserum derived from the mammals immunized with the above-mentioned monoclonal antibody (for example monoclonal antibody #72-1, #86-2 or #176-1) or antibody fragment F(ab')$_2$ or Fab' of these antibodies.

"Insoluble carrier" of the present invention means a carrier for carrying human CETP in a sample(for example, body fluid sample such as blood plasma, culture supernatant or centrifuge supernatant) or for carrying the above-mentioned monoclonal antibody or the antibody fragment, for example, by physical adsorption or a chemical bond. For examples, the following can be used; (1) plastics composed of polystyrene resin, polycarbonate resin, silicon resin or nylon resin; a plate composed of water insoluble substances such as glass; a test tube or tube having an inner capacity; beads; a ball; a filter or a membrane etc., and (2) insoluble carriers used for affinity chromatography such as a cellulose type carrier, an agarose type carrier, a polyacrylamide type carrier, a dextran type carrier, a polystyrene type carrier, a polyvinyl alcohol type carrier, a poly amino acid type carrier and a porous silica type carrier.

"Immobilized monoclonal antibody" or "immobilized antibody fragment" of the present invention means a monoclonal antibody or an antibody fragment which is bound to said insoluble carrier by physical adsorption or a chemical bond. The immobilized monoclonal antibody or the immobilized antibody fragment can be used for detection, assay, separation and purification of human CETP in a sample(for example, a body fluid sample such as blood plasma, culture supernatant and centrifugation supernatant). For the purpose of detection or assay, the immobilized monoclonal antibody or the immobilized antibody fragment immobilized on the insoluble carrier mentioned as (1) above can be used. Especially for the assay, considering simple handling and simultaneous handling of many samples, it is preferable to use a plastic plate having many wells such as a microtiter plate with 96 wells. For separation and purification, the immobilized monoclonal antibody or immobilized antibody fragment immobilized on a filter or membrane mentioned as (1) above or the insoluble carrier mentioned as (2) above can be used.

"Labeling substance capable of providing detectable signals independently or by reaction with another substance" of the present invention means a substance which is used to detect the above-mentioned monoclonal antibody, the antibody fragment or the human CETP standard. They are detectable by binding the substance with the antibody, the fragment or the standard (physicochemical binding etc.). Specifically, the substance is either an enzyme, a fluorescent material, a chemical luminous material, biotin, avidin or a radioisotope, and so forth. More specifically, the substance is an enzyme such as peroxidase, alkaline phosphatase, β-D-galactosidase, glucose oxidase, glucose-6-phosphate dehydrogenase, alcohol dehydrogenase, malate dehydrogenase, penicillinase, catalase, apo-glucose oxidase, urease, luciferase and acetylcholine esterase; a fluorescent material such as a fluorescent isothiocyanate, phycobilin protein, a rare earth metal chelate, dansylchloride and tetramethylrhodamine isothiocyanate; a radioisotope such as $^3$H, $^{14}$C and $^{131}$I; biotin; avidin or a chemical luminous material.

Radioisotopes and fluorescent materials can provide detectable signals independently. On the other hand, enzymes, chemical luminous materials, biotin and avidin cannot provide detectable signals independently, but with one or more other substance(s), they can provide detectable signals. For instance, in the case of an enzyme, it requires at least its substrate. Various substrates are used depending on the method for measuring enzyme activity(colorimetric method, fluorescence method, bioluminescence method or chemical luminescence method etc.). In the case of biotin, generally, it is reacted with, at least, avidin or enzymatically modified avidin, but it is not limited to this method. If necessary, various coloring developing substances depending on said substrates can be used.

"Labeled monoclonal antibody", "labeled antibody fragment" and "labeled human CETP standard" of the present invention mean the monoclonal antibody, the antibody fragment and the human CETP standard labeled with the labeling substance, respectively. These labeled monoclonal antibody, labeled antibody fragment and labeled human CETP standard can be used for detection and assay of human CETP in a sample such as a body fluid sample(blood plasma etc., culture supernatant and centrifugation supernatant). In the present invention, any labeling substance mentioned above can be used, however, considering the detection limit(sensitivity), assay limit and handling(convenience), biotin labeling is preferable.

"Human CETP standard" of the present invention means human CETP used as a standard for the detection or assay of human CETP in a sample as mentioned above.

"Immunoassay" of the present invention means a method for detection or assay of an antigen contained in a sample(for example, a body fluid sample such as blood plasma, culture supernatant or centrifugation supernatant) based on the principle of antigen-antibody reaction. Any known immunoassay methods can be applied to the present invention as long as the antibody used for the antigen-antibody reaction is one or more of the monoclonal antibody or antibody fragments selected from the above-mentioned monoclonal antibody or its antibody fragment, the above-mentioned immobilized monoclonal antibody or the immobilized antibody fragment or the above-mentioned labeled monoclonal antibody or the labeled antibody fragment, and as long as the antigen is human CETP.

Specifically, the methods exemplified are described in "Enzyme Immuno Assay"(3rd edition, Eiji Ishikawa et al. ed., Igakusyoin, 1987) such as single antibody solid phase method, double antibody liquid phase method, double antibody solid phase method, sandwich method, enzyme multiplied immunoassay technique(EMIT), enzyme channeling immunoassay, Enzyme modulator mediated enzyme immunoassay (EMMIA), enzyme inhibitor immunoassay, immunoenzymometric assay, enzyme enhanced immunoassay and proximal linkage immunoassay, or one pot method as described in Japanese Patent Publication No. HEI2-39747.

In the present invention, depending on the purpose of the assay, an appropriate immunoassay can be selected. Considering the ease of handling and/or economic efficiency, especially in consideration of their wide clinical use, the sandwich method, one pot method, single antibody solid phase method or double antibody liquid phase method is preferable. It is more preferable to use the sandwich method or the one pot method. It is most preferable to use the sandwich method using the immobilized monoclonal antibody or the immobilized antibody fragment immobilized on a microplate having many wells such as a 96 well microplate and the labeled monoclonal antibody or the labeled antibody fragment labeled with an enzyme or biotin, or the one pot method using the immobilized monoclonal antibody or the immobilized antibody fragment immobilized on beads or a ball and the labeled monoclonal antibody or labeled antibody fragment labeled with an enzyme or biotin.

A specific example of the most preferable embodiment is the sandwich method or the one pot method using the following combination, the monoclonal antibody #72-1, #86-2 or #176-1, or their F(ab')2 or Fab' immobilized on a microplate, beads or ball and with the monoclonal antibody #72-1, #86-2 or #176-1 or their F(ab')2 or Fab' labeled with an enzyme or biotin. Although the monoclonal antibodies #72-1, #86-2 or #176-1 can be used in immobilized form as well as in labeled form, it is preferable to use #72-1 in immobilized form and #86-2 or #176-1 in labeled form.

Particularly, it is more preferable to use monoclonal antibody #72-1 (which is the monoclonal antibody derived from the hybridoma identified with FERM BP4944) as the immobilized monoclonal antibody and monoclonal antibody #86-2 (which is the monoclonal antibody derived from the hybridoma identified with FERM BP4945) as the labeled one.

Details of the sandwich method, one pot method, single antibody solid phase method, double antibody liquid phase method are described below.

The sandwich method is a method described in the first part of the tenth aspect of the present invention, i.e., an immunoassay comprising at least the following steps:
(a) reacting a sample with the immobilized monoclonal antibody or the immobilized antibody fragment of the present invention; and
(b) reacting the labeled monoclonal antibody or the labeled antibody fragment with the antigen-antibody complex formed by binding human CETP in a sample with the immobilized monoclonal antibody or the immobilized antibody fragment.

Based on the present invention, most conventional methods using an enzyme or biotin as a labeling substance are described in detail below. Those methods comprise the following steps but are not limited to the following examples. The terms of "Immobilized monoclonal antibody" and "monoclonal antibody-immobilized microplate" used below have the same meaning.
(Step 1) a step for preparing an immobilized monoclonal antibody(monoclonal antibody-immobilized microplate) by immobilizing the monoclonal antibody #72-1, #86-2 or #176-1 reactive to human CETP of the present invention on a microplate;
(Step 2) a step to react a sample with the immobilized monoclonal antibody by adding a sample such as human blood plasma to the monoclonal antibody-immobilized microplate;
(Step 3) a step to remove the non-reacted sample from the immobilized antibody by washing the monoclonal antibody immobilized microplate;
(Step 4) a step to prepare a labeled monoclonal antibody by labeling the monoclonal antibody #72-1, #86-2 or #176-1 reactive to human CETP of the present invention with biotin or an enzyme such as peroxidase;
(Step 5) a step to react the labeled monoclonal antibody with an antigen-antibody complex (formed by reacting the immobilized monoclonal antibody with human CETP in a sample) by adding the labeled monoclonal antibody to the monoclonal antibody-immobilized microplate washed by "Step 3";
(Step 6) a step to remove the non-reacted labeled monoclonal antibody with the antigen-antibody complex by washing the monoclonal antibody-immobilized microplate;
(Step 7) a step to add avidin or enzyme-modified avidin (when a biotin labeled monoclonal antibody was used at "Step 4"), or to add various substrates, depending on the method used for measuring enzyme activity (when enzyme-labeled monoclonal antibody labeled by such as peroxidase was used at "Step 4" together with a coloring agent(if necessary), to the monoclonal antibody-immobilized microplate (washed at "Step 6") and to react with labeling substance on the labeled monoclonal antibody;
(Step 8) a step to react an avidin-bound enzyme with a substrate by adding various substrates depending on the method for measuring enzyme activity when enzyme-modified avidin is used in "Step 7";
(Step 9) a step to stop the coloring reaction and enzymatic reaction by adding a stop solution to the monoclonal antibody-immobilized microplate; and
(Step 10) a step to measure the intensity of coloring, fluorescence or luminescence.

Although the monoclonal antibodies #72-1, #86-2 or #176-1 can be used in immobilized form as well as in labeled form, it is preferable to use #72-1 in immobilized form, and #86-2 or #176-1 (preferably, #86-2) in labeled form.

The one pot method is an immunoassay mentioned in the first, the second or the third part of the tenth aspect of the present invention. The first part is an immunoassay including at least the following steps:
(a) reacting sample with the immobilized monoclonal antibody or the immobilized antibody fragment of the present invention; and
(b) reacting the labeled monoclonal antibody or the labeled antibody fragment with an antigen-antibody complex formed by binding human CETP in a sample with the immobilized monoclonal antibody or the immobilized antibody fragment.

The second part is an immunoassay including at least the following steps:
(a) reacting a sample with the labeled monoclonal antibody or the labeled antibody fragment of the present invention; and
(b) reacting the immobilized monoclonal antibody or the immobilized antibody fragment of the present invention with the antigen-antibody complex formed by binding human CETP in a sample with the labeled monoclonal antibody or the labeled antibody fragment.

The third part is an immunoassay comprising at least the following step:
(a) reacting a mixture comprising the immobilized monoclonal antibody or the immobilized antibody fragment of the present invention, the labeled monoclonal antibody or the labeled antibody fragment of the present invention and a sample.

Based on the present invention, the above-mentioned three aspects are described in detail by describing a more common method using an enzyme as a labeling agent, which comprises the following steps. However, the present invention is not limited to such examples given below. The terms of "immobilized monoclonal antibody" and "monoclonal antibody-immobilized beads" have the same meaning.

The first method comprises the following steps:
(Step 1) A step for preparing immobilized monoclonal antibodies (monoclonal antibody-immobilized beads) by immobilizing monoclonal antibody, #72-1, #86-2, or #176-1 which is reactive to human CETP of the present invention, on the beads;
(Step 2) a step for reacting an analyte in a sample with the immobilized monoclonal antibody by adding both the monoclonal antibody-immobilized beads and the sample such as human plasma together with a buffer solution into a container having an inner capacity such as a test tube, plate or tube;
(Step 3) a step for removing the solution in the container and washing the monoclonal antibody-immobilized beads;
(Step 4) a step for producing a labeled monoclonal antibody by labeling monoclonal antibody of the present invention, #72-1, #86-2, or #176-1, which is reactive to human CETP, with biotin or an enzyme such as peroxidase,
(Step 5) a step for reacting the labeled monoclonal antibody with an antigen-antibody complex formed by reaction of the immobilized monoclonal antibody with human CETP in a sample, by adding the labeled monoclonal antibody into the container containing the monoclonal antibody-immobilized beads washed in Step 3;
(Step 6) a step for removing the labeled monoclonal antibody which has not reacted with the complex from the container by removing the solution in the container and by washing the monoclonal antibody-immobilized beads;
(Step 7) a step to add avidin or enzyme-modified avidin (when a biotin-labeled monoclonal antibody was used at "Step 4"), or to add various substrates, depending on the method used for measuring enzyme activity (when enzyme-labeled monoclonal antibody labeled by such as peroxidase was used at "Step 4" together with a coloring agent(if necessary), to the monoclonal antibody-immobilized beads (washed at "Step 6") and to react with the labeling substance on the labeled monoclonal antibody;
(Step 8) a step to react an avidin-bound enzyme with a substrate by adding various substrates depending on the method for measuring enzyme activity when enzyme-modified avidin is used in "Step 7";
(Step 9) a step for terminating both the enzyme reaction and color development by adding a terminator solution into either the reaction mixture of Step 7 or 8; and
(Step 10) a step for determining the calorimetric intensity, fluorescence intensity or luminescence intensity.

The second method comprises the following steps:
(Step 1) a step for preparing labeled monoclonal antibody by labeling the monoclonal antibody of the present invention which is reactive to human CETP, #72-1, #86-2, or #176-1, with a labeling substance such as biotin or an enzyme such as peroxidase;
(Step 2) a step for reacting a sample with the labeled monoclonal antibody by adding both the labeled monoclonal antibody and the sample solution such as human plasma together with a buffer solution into a container having an inner capacity such as a test tube, plate or tube;
(Step 3) a step for preparing an immobilized monoclonal antibody(monoclonal antibody-immobilized beads) by immobilizing the monoclonal antibody of the present invention which is reactive to human CETP, #72-1, #86-2, or #176-1, onto the beads;
(Step 4) a step for reacting the immobilized monoclonal antibody with the antigen-antibody complex formed by the reaction of the labeled monoclonal antibody with the human CETP in the sample, by adding the monoclonal antibody-immobilized beads in the reaction mixture of Step 2;
(Step 5) a step for removing the labeled monoclonal antibody which has not reacted with the complex by removing the solution in the container and by washing the monoclonal antibody-immobilized beads;
(Step 6) a step to add avidin or enzyme-modified avidin (when a biotin labeled monoclonal antibody was used at "Step 1"), or to add various substrates, depending on the method used for measuring enzyme activity (when enzyme-labeled monoclonal antibody labeled by such as peroxidase was used at "Step 1" together with a coloring agent(if necessary), to the monoclonal antibody-immobilized beads (washed at "Step 5") and to react with labeling substance on the labeled monoclonal antibody;
(Step 7) a step to react an avidin-bound enzyme with a substrate by adding various substrates depending on the method for measuring enzyme activity when enzyme-modified avidin is used in "Step 6";
(Step 8) a step for terminating both the enzyme reaction and color development by adding a terminator solution into either the reaction mixture of Step 6 or 7; and
(Step 9) a step for determining the calorimetric intensity, fluorescence intensity or luminescence intensity.

The third method comprises the following steps:
(Step 1) a step for preparing immobilized monoclonal antibody(monoclonal antibody-immobilized beads) by immobilizing the monoclonal antibody of the present invention which is reactive to human CETP, #72-1, #86-2, or #176-1, onto the beads;
(Step 2) a step for preparing labeled monoclonal antibody by labeling the monoclonal antibody which is reactive to human CETP, #72-1, #86-2, or #176-1, with biotin or an enzyme such as peroxidase;
(Step 3) a step for simultaneously reacting the sample with both the immobilized monoclonal antibody and the labeled monoclonal antibody by adding all of the monoclonal antibody-immobilized beads prepared in Step 1, the labeled monoclonal antibody prepared in Step 2, and the sample solution such as human plasma together with a buffer solution into a container having an inner capacity such as a test tube, plate or tube;
(Step 4) a step for removing the unreacted labeled monoclonal antibody which has not reacted with the complex by removing the solution in the container and by washing the monoclonal antibody-immobilized beads;
(Step 5) a step to add avidin or enzyme-modified avidin (when a biotin labeled monoclonal antibody was used at "Step 2"), or to add various substrates, depending on the method used for measuring enzyme activity (when enzyme-labeled monoclonal antibody labeled by such as peroxidase was used at "Step 2" together with a coloring agent(if necessary), to the monoclonal antibody-immobilized beads (washed at "Step 4") and to react with labeling substance on the labeled monoclonal antibody;

(Step 6) a step to react an avidin-bound enzyme with a substrate by adding various substrates depending on the method for measuring enzyme activity when enzyme-modified avidin is used in "Step 5";

(Step 7) a step for terminating both the enzyme reaction and color development by adding a terminator solution into either the reaction mixture of Step 5 or 6; and (Step 8) a step for determining the calorimetric intensity, fluorescence intensity or luminescence intensity.

In the above-mentioned method 1 to 3, any of the monoclonal antibodies, #72-1, #86-2, and #176-1 may be employed as immobilized and labeled monoclonal antibody. However, monoclonal antibody #72-1 is preferable as the immobilized monoclonal antibody, and both the monoclonal antibodies #86-2 and #176-1 are preferable as labeled monoclonal antibodies. The monoclonal antibody #86-2 is more preferable as labeled monoclonal antibodies.

A single antibody solid phase method is described above in the fourth part of the tenth aspect of the present invention, and it is an immunoassay comprising at least the following step:

(a) reacting a sample and a labeled human CETP standard labeled with a labeling substance capable of providing detectable signals independently or by reaction with other substances with the immobilized monoclonal antibody or the immobilized antibody fragment of the present invention.

According to the present invention, the method which employs the labeling substance, particularly a commonly used enzyme or biotin as the labeling substance, is explained in detail hereinbelow. For instance, the method comprises the following steps. The present invention is not limited to the example. Furthermore, "immobilized monoclonal antibody" and "monoclonal antibody-immobilized microplate" have the same meaning.

(Step 1) A step for preparing immobilized monoclonal antibody(monoclonal antibody-immobilized microplate) by immobilizing the monoclonal antibody of the present invention which is reactive to human CETP, #72-1, #86-2, or #176-1, onto the microplate;

(Step 2) a step for preparing a labeled human CETP standard by labeling the human CETP standard with biotin or an the enzyme such as a peroxidase;

(Step 3) a step for competitively reacting both the sample such as human plasma and the human CETP standard with the immobilized monoclonal antibody in the monoclonal antibody-immobilized microplate;

(Step 4) a step for removing the labeled human CETP standard which has not reacted with the immobilized antibody by washing the monoclonal antibody-immobilized microplate;

(Step 5) a step to add avidin or enzyme-modified avidin (when a biotin labeled monoclonal antibody was used at "Step 2"), or to add various substrates, depending on the method used for measuring enzyme activity (when enzyme-labeled monoclonal antibody labeled by such as peroxidase was used at "Step 2" together with a coloring agent(if necessary), to the monoclonal antibody-immobilized beads (washed at "Step 4") and to react with a labeling substance on the labeled monoclonal antibody;

(Step 6) a step to react an avidin-bound enzyme with a substrate by adding various substrates depending on the method for measuring enzyme activity when enzyme-modified avidin is used in "Step 5";

(Step 7) a step for terminating both the enzyme reaction and color development by adding a terminator solution into the monoclonal antibody-immobilized microplate; and (Step 8) a step for determining the calorimetric intensity, fluorescence intensity or luminescence intensity.

The monoclonal antibody #72-1, #86-2, or #176-1 may be used as the immobilized monoclonal antibody, however, the monoclonal antibody #72-1 is preferable for this purpose.

The double antibody liquid phase method is described in the fifth part of the tenth aspect of the present invention, and it is an immunoassay comprising at least the following step (a) or the following steps (b) and (c):

(a) reacting the monoclonal antibody or antibody fragment of the present invention with a mixture of a sample and the labeled human CETP standard labeled with a labeling substance capable of providing detectable signals independently or by reaction with other substances; or (b) reacting the monoclonal antibody or the antibody fragment of the present invention with the sample; and (c) followed by step (b), reacting the labeled human CETP standard labeled with a labeling substance capable of providing detectable signals independently or by reaction with other substances; or with the reaction mixture of step (b).

More specifically, the method is an immunoassay comprising at least the following steps of (a) and (d), or steps (b) to (d).

(a) reacting the monoclonal antibody or the antibody fragment of the present invention with a mixture of a sample and the labeled human CETP standard labeled with a labeling substance capable of providing detectable signals independently or by reaction with other substances;

(b) reacting the monoclonal antibody or the antibody fragment of the present invention with the sample;

(c) followed by step (b), reacting the labeled human CETP standard labeled with a labeling substance capable of providing detectable signals independently or by reaction with another substance; with the reaction mixture of step (b);

(d) reacting an antiserum derived from a mammal reactive to the monoclonal antibody or the antibody fragment with an antigen-antibody complex formed by binding human CETP in the sample or the labeled human CETP standard with the monoclonal antibody or the antibody fragment.

According to the present invention, the procedure which employs the labeling substance, particularly a commonly use d enzyme or biotin as the labeling substance, is explained in detail hereinbelow. For instance, the procedure comprises the following steps; however, the present invention is not limited to the example.

(Step 1) A step for preparing a labeled human CETP standard by labeling the human CETP standard with biotin or an enzyme such as a peroxidase;

(Step 2) a step for (1) adding a mixture comprising a sample such as human plasma and the labeled human CETP standard prepared in the above Step 1 into a container having an inner capacity such as a test tube, plate, or tube, and subsequently adding the monoclonal antibody of the present invention, #72-1, #86-2, or #176-1 which is reactive to the human CETP, and competitively reacting the sample and the labelled human CETP standard with the monoclonal antibody of the present invention, #72-1, #86-2, or #176-1; or (2) a step for adding the sample such as human plasma into a container having an inner capacity such as a test tube, plate, or tube and subsequently adding the monoclonal antibody of the present invention, #72-1, #86-2, or #176-1, which is reactive to human CETP and reacting the sample with the above antibody, #72-1, #86-2, or #176-1;

(Step 3) a step to add a labeled human CETP standard when the labelled human CETP was not added simultaneously in the above step 2 (namely, (2)) to react the monoclonal antibody of the present invention, #72-1, #86-2, or #176-1, with the labeled human CETP standard;

(Step 4) a step for adding antiserum derived from a mammal other than mouse which is reactive to a mouse monoclonal antibody, such as anti-mouse γ globulin goat serum to react with the antigen-antibody complex formed by binding the monoclonal antibody, #72-1, #86-2, or #176-1, prepared in Step 2 to 3 with either human CETP in the sample or with the labeled human CETP standard; and precipitating the agglutinate complex comprising three components: the monoclonal antibody the present invention, of #72-1, #86-2, or #176-1, the human derived CETP in the sample or the labeled human CETP standard, and the antiserum derived from a mammal other than mouse;

(Step 5) a step for removing the agglutinate complex precipitated by centrifugation of the reaction mixture in Step 4;

(Step 6) a step to add avidin or enzyme-modified avidin (when a biotin labeled CETP standard derived from human was used at "Step 1"), or to add various substrates, depending on the method used for measuring enzyme activity (when enzyme-labeled CETP standard derived from human labeled by such as peroxidase was used at "Step 1" together with a coloring agent(if necessary), to the agglutinate complex (separated at "Step 5") and to react with labeling substance on the CETP standard derived from human;

(Step 7) a step to react an avidin-bound enzyme with a substrate by adding various substrates depending on the method for measuring enzyme activity when enzyme-modified avidin is used in "Step 6";

(Step 8) a step for terminating both the enzyme reaction and color development by adding a terminator solution into either the reaction mixture of Step 6 or Step 7; and (Step 9) a step for determining the calorimetric intensity, fluorescence intensity or luminescence intensity.

Any of the monoclonal antibody #72-1, #86-2, or #176-1 may be used in the above-mentioned examples, however, the monoclonal antibody #72-1 is prefered.

The term "affinity chromatography" in the present invention means chromatography for separation or purification of human CETP contained in a sample by using the affinity between the antigen and antibody. As the examples of a sample, body fluids such as plasma, culture supernatants, or centrifugation supernatants are given. Specifically, the following methods are given as examples.

(1) A method for separating the human CETP in the sample comprises applying the sample to the above-mentioned insoluble carrier such as a filter or a membrane on which a monoclonal antibody or its fragment of the present invention, which is reactive to human CETP, has been immobilized to separate the human CETP.

(2) A method for separating or purifying the human CETP in the sample, comprises immobilizing a monoclonal antibody or its fragment of the present invention which is reactive to human CETP, to the above-mentioned insoluble carrier (e.g., a cellulose type carrier, an agarose type carrier, a polyacrylamide type carrier, a dextran type carrier, a polystyrene type carrier, a polyvinyl alcohol type carrier, a polyamino acid type carrier and a porous silica type carrier) by known methods (such as physical adsorption, polymerization by cross-linking, trapping in the carrier matrix, or immobilization by non-covalent bonding), filling the insoluble carrier into a column such as a glass, plastic or stainless column having a cylindrical configuration, and applying a sample (e.g., a body fluid such as blood plasma, a culture supernatant, or a centrifugation supernatant) into the column for elution. Particularly, the latter method of (2) is referred to as affinity column chromatography here.

As for the insoluble carriers for affinity chromatography, any type carrier may be used as long as they can immobilize the monoclonal antibody or its fragment of the present invention on them. As examples, commercially available carriers such as SEPHAROSE 2B, SEPHAROSE 4B, SEPHAROSE 6B, CNBr-SEPHAROSE 4B, AH-SEPHAROSE 4B, CH-SEPHAROSE 4B, ACTIVATED CH-SEPHAROSE 4B, EPOXY-ACTIVATED SEPHAROSE 6B, ACTIVATED THIOL-SEPHAROSE 4B, SEPHADEX, CM-SEPHADEX, ECH-SEPHAROSE 4B, EAH-SEPHAROSE 4B, NHS-ACTIVATED SEPHAROSE, THIOPROPYL SEPHAROSE 6B, and so forth (Pharmacia); BIO-GEL A, CELLEX, CELLEX AE, CELLEX-DM, CELLEX PAB, BIO-GEL-P, HYDRAZIDE BIO-GEL P, AMINOETHYL BIOGEL P, BIO-GEL CM, AFFI-GEL 10, AFFI-GEL 15, AFFI-PREP 10, AFFI-GEL Hz, AFFI-PREP Hz, AFFI-GEL 102, CM BIO-GEL A, AFFI-GEL HEPARIN, AFFI-GEL 501, or AFFI-GEL 601, and so forth (Bio-Rad); CHROMA-GEL A, CHROMA-GEL P, ENZAFIX P-Hz, ENZAFIX P-SH, ENZAFIX P-AB, and so forth (Wako Pure Chemicals); Ae-CELLULOSE, CM-CELLULOSE, PAB CELLULOSE, and so forth(Serva) are given.

"Mice having introduced DNA encoding human CETP" may be produced by techniques employed generally in the field of transgenic mouse production(See, The Newest Animal Cell Experiment Manual, LIC press, Chapter 7, pp. 361–408, 1990).

Tall et al. reported that they were able to produce a transgenic mouse in which a human CETP gene has been introduced. However, the mouse cannot secrete CETP in blood unless it receives extrinsic or artificial induction such as receiving food supplemented with zinc. In contrast, the transgenic mouse of the present invention constantly secretes human CETP in blood without any artificial induction described above, and such a transgenic mouse has not been reported previously.

A "pharmaceutical composition" comprises the monoclonal antibody or its fragment of the present invention as an active ingredient, and may further comprise one or more pharmaceutically acceptable carrier(s) such as excipients, diluents, vehicles, disintegrators, stabilizers, preservatives, buffering agents, emulsifiers, aromatics, coloring agents, sweetening agents, thickning agents, flavoring agents, solubilizing agents, and other additives. Such a pharmaceutical composition may be formed as tablets, pills, powders, granules, injections, liquid preparations, capsules, troches, elixirs, suspensions, emulsions, or syrups. The pharmaceutical composition may be administrated orally or parentally.

In particular, injections may be prepared by dissolving or suspending the monoclonal antibody or its fragment of the present invention in a pharmaceutically acceptable carrier without toxicity at a concentration from 0.1 $\mu$g of the monoclonal antibody/ml of carrier to 10 mg of the antibody/ml of carrier such as physiological saline, and distilled water for injections. Such injections may be administrated to patients who need treatments at dosages of 1 $\mu$g to 100 mg/kg of body weight, preferably at 50 $\mu$g to 50 mg/kg of body weight from one to several times per day. This administration is performed via clinically suitable routes such as intravenously, subcutaneously, intradermally, intramuscularly, in intraperitoneally and so forth. Preference is given to intravenous administration.

The pharmaceutical composition of the present invention may be applicable not only for treating or preventing hyperlipidemia but also for treating or preventing various diseases such as arteriosclerosis caused by the abnormal kinetics of CETP, hyperalphalipoproteinemia and hypercholesterolemia.

EXAMPLES

The present invention is illustrated explained in detail hereinbelow based on the following working Examples. However, the present invention is not limited to such examples.

Example 1

Establishment of CETP Activity Assay System

In the present invention, the determination of the CETP activity (cholesterol ester(abbreviated as CE) transporting activity) was conducted using the assay system constructed as described below unless specially stated. The assay system of the present invention is a modified one according to the method of Alberts et al., Arteriosclerosis, vol. 4, 49–58 (1984). Briefly, the assay system was as follows. First, a donor lipoprotein comprising high density lipoprotein ($HDL_3$) in which radio-labeled cholesterol ester was incorporated, an acceptor lipoprotein comprising low density lipoprotein (LDL), and a sample containing CETP for assay were mixed to physiologically react with each other. Then, the amount of labeled CE transported from the donor lipoprotein to the acceptor lipoprotein was determined by measuring either the decrease of the radioactivity of the donor lipoprotein or increase of that of the acceptor lipoprotein to determine CETP transporting activity of CETP in the sample.

<1-1> Preparation of Donor Lipoprotein

Potassium bromide(KBr) was added to 20 ml of healthy volunteer plasma to adjust its specific gravity, d=1.125 g/ml. After that, the plasma was subjected to density gradient centrifugation at 227,000×g at 4° C. for 17 hours, and then a fraction was obtained of which the specific gravity was d>1.125 g/ml($HDL_3$ fraction). This fraction was dialyzed against TBS(0.15 M NaCl/10 mM Tris(pH 7.4)). Then, 10 nM of tritium labeled cholesterol($[^3H]C$, specific activity 50.3 Ci/mM) dissolved in 95% ethanol was gradually added with slow stirring. The solution was incubated for 18 hr at 37° C. During the incubation, tritium labelled cholesterol ($[^3H]C$) on the surface of $HDL_3$ was esterified by Lecithin Cholesterol Acyltransferase(LCAT) to be converted to tritium labeled cholesterol ester($[^3H]CE$). Then $[^3H]CE$ was incorporated into $HDL_3$.

KBr was added to the solution to adjust its specific gravity, d=1.21 g/ml. After that, the solution was subjected to density gradient centrifugation at 227,000×g at 4° C. for 20 hours, and then a fraction was obtained of which the specific gravity was d<1.21 g/ml. The fraction obtained was dialyzed against TBS as described before, and then $HDL_3$ incorporating $[^3H]CE$($[^3H]CE$-$HDL_3$; specific gravity was 1.125<d<1.21; specific activity was 101,000 dpm/nM) was obtained. This fraction was used as a donor lipoprotein.

<1-2> Preparation of Acceptor Lipoprotein

Potassium bromide(KBr) was added to 100 ml of healthy volunteer plasma to adjust its specific gravity, d=1.019 g/ml. After that, the plasma was subjected to density gradient centrifugation at 227,000×g at 4° C. for 20 hours, and then the fraction of which the specific gravity was d>1.019 g/ml was obtained. The fraction obtained was dialyzed against TBS as described above. Then, KBr was added again to adjust the specific gravity to d=1.063 g/ml. The solution was subjected to density gradient centrifugation at 227,000×g at 4° C. for 20 hr, and then a fraction was obtained with d<1.063 g/ml. The fraction obtained was dialyzed against TBS as described above, and then the fraction comprising LDL(specific gravity:1.019<d<1.063) was obtained to be used as acceptor lipoprotein.

<1-3> Determination of CETP activity

The donor lipoprotein obtained in Example <1-1>($[^3H]$ CE-$HDL_3$ which contains 0.21 μg of cholesterol), the acceptor lipoprotein(LDL which contains 21 μg of cholesterol), and a sample for assay were mixed in a microtube. Then, TBS as described above was also added to the microtube to adjust the ratio of cholesterol content in the donor lipoprotein to that in the acceptor lipoprotein to 1:100, and to adjust the ratio of cholesterol in HDL contained in the assay sample to that in the donor lipoprotein to at least 1:10(total volume is 600 μl/tube). The tube was incubated for 15 hr in a water bath at 37° C. Then, the tube was transferred onto ice for 15 minutes. After that, 400 μl of iced TBS and 40 μl of 1% dextran sulfate solution containing 0.5 M $MgCl_2$ were added into the microtube, and the microtube was vigorously vortexed. The microtube was incubated for 30 minutes on ice. Then, the tube was subjected to centrifugation at 8,000×g at 4° C. for 10 minutes, and then HDL rich supernatant was recovered. The radioactivity in the centrifugation supernatant was measured by means of a scintillation counter.

In order to determine the CETP activity of the assay sample containing CETP, the radioactivity of the control sample which does not contain the assay sample was also measured by treating it in the same manner as in the procedure described above. The CETP activity was determined by the decrease of radioactivity based on the comparison of the value measured for the assay samples to that for the control sample. The activity was expressed in units, and the CETP activity for transporting 1 nM of cholesterol per one unit time was represented as 1 unit(U).

Example 2

Preparation of Purified Human-derived CETP

The procedure described below was performed at 4° C. or in an ice bath according to a known method.

<2-1> Dextran Sulfate Treatment

Peripheral blood was obtained from healthy volunteers. Red blood cells in the blood were removed by centrifugation by a known method, and then 1 L of human plasma was obtained. Two liters of distilled water, 100 ml of 10% dextran sulfate molecular weight of 500,000 Da 100 ml), and 80 ml of 4 M $CaCl_2$ were added to the obtained plasma and gently stirred in an ice bath for 15 minutes. The mixed solution was centrifuged at 15,200×g for 1 hr to fractionate insoluble dextran sulfate/lipoprotein complex as precipitate. The supernatant was collected, and 27.2% $BaCl_2$ was added to adjust the final concentration of the solution to 1.36%. The mixed solution was stirred for 20 minutes, and then centrifuged at 15,200×g for 1 hr. The precipitate was removed, and the supernatant was collected. <2-2> Purification by PHENYL SEPHAROSE Column Chromatography Three molar NaCl, 0.01% sodium azide($NaN_3$), 50 μg/ml of gentamycin sulfate, and 0.05% ethylenediamine tetraacetic acid(EDTA) were added into the supernatant obtained in Example<2-1>. The mixture was adjusted to pH 7.4. A PHENYL SEPHAROSE HP column(10×12.5 cm, Pharmacia Biotech) was equilibrated with 3 M NaCl(pH 7.4) containing 0.01% $NaN_3$, 50 μg/ml gentamycin sulfate, and 0.05% EDTA as mentioned above. The mixture was applied onto the PHENYL SEPHAROSE column. After that the column was washed with 3 L of 0.15 M NaCl solution(pH 7.4), subsequently with 3 L of the solution without NaCl(pH 7.4), and then eluted with 20% ethanol. The elution profile was monitored by measuring the absorbance at 280 nm.

The result is shown in FIG. 1. Based on the elution profile, active fractions containing human-derived CETP were collected.

<2-3> Purification by Means of RESOURCE Q Column Chromatography

The active fractions collected in Example<2-2>were dialyzed against a buffer(pH 7.4) comprising 25 mM NaCl and 10 mM Tris-HCl. Then, the dialyzed fraction was applied onto a RESOURCE Q column(3.5×10 cm, Pharmacia Biotech) equilibrated with the buffer. The column was washed with 300 ml of the above-mentioned buffer, and eluted with 2 L of 25–250 mM gradient NaCl(pH 7.4). The elution profile was monitored by measuring the absorbance at 280 nm.

Figure 2:
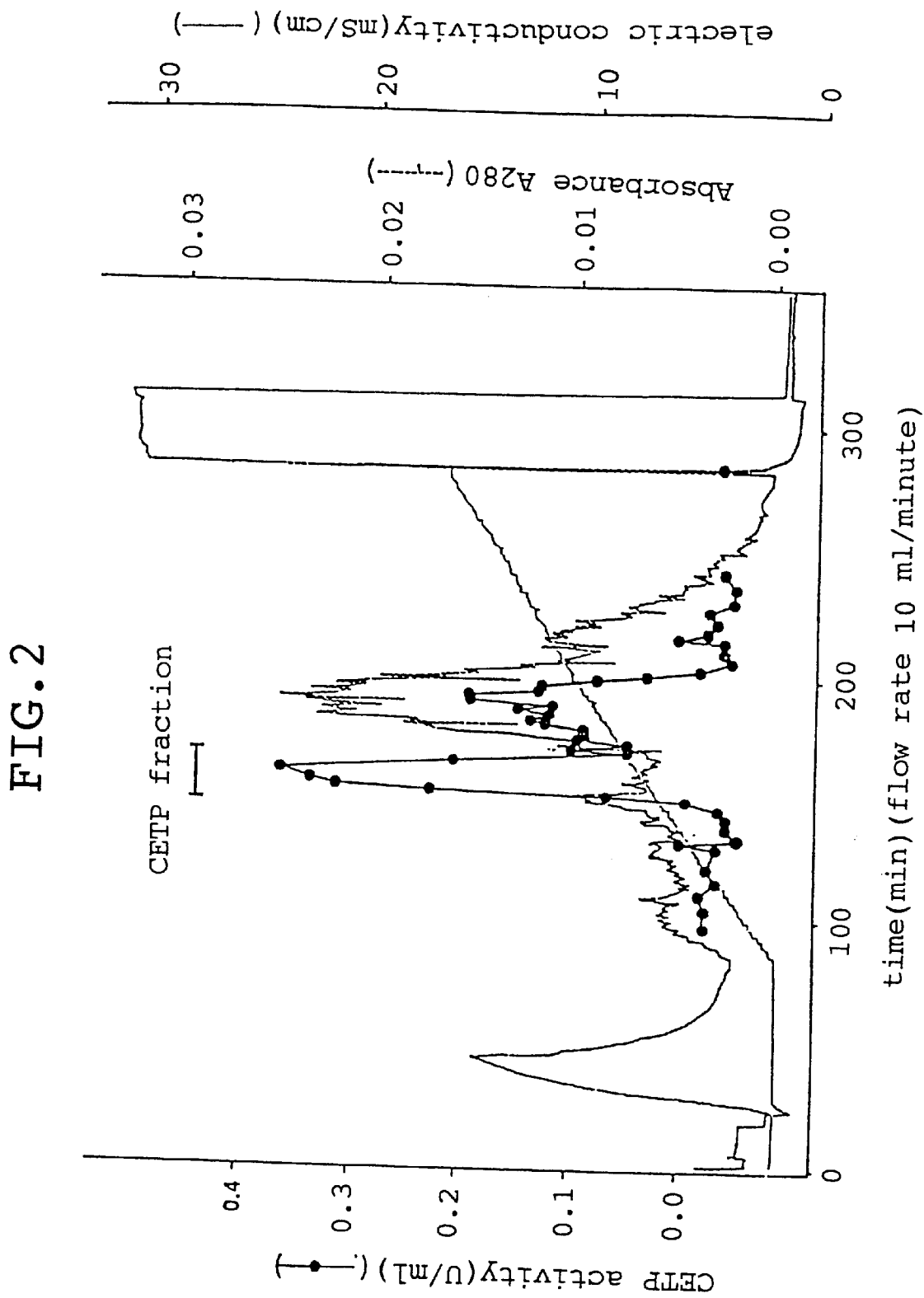
FIG. 2 shows a chromatogram of human CETP by RESOURCE Q column chromatography.

The result is shown in FIG. 2. Based on the elution profile, active fractions containing human-derived CETP were collected to obtain purified human CETP.

Example 3

Preparation of Anti-human CETP Monoclonal Antibodies

Anti-human CETP monoclonal antibodies were prepared according to a known method described in references such as Experimental Medicine, suppl. "Cell Engineering Handbook" (Toshio Kuroki et al. ed., pp. 66–74, Yodo press (1992)) or "An Introduction to Monoclonal Antibody Experimental Procedure" (Tamio Ando et al., Kodansha (1991)).

<3-1> Immunization, Cell Fusion, and Cloning

Purified human CETP prepared in Example 2 with Freund's complete adjuvant was injected into the foot pads of BALB/c mice(female, 4–5 week age, purchased from Shizuoka experimental animal center) for the first immunization. On the 5th, 10th, and 15th day after the first immunization, the purified human CETP was injected into the foot pads of the immunized mice as an additional immunization. Furthermore, purified human CETP was given similarly to the mice as a final immunization one and two days before the preparation of hybridomas which produce monoclonal antibodies. Lymph nodes of the knee were excised from the mice by a surgical operation according to known methods. The lymphocytes obtained from the lymph node and mouse myeloma cells, PAI, were mixed at the ratio of 3:1, and fused by using polyethylene glycol 4000 as a fusion agent (at the ratio of 3:1) to produce hybridomas. Then, the hybridomas were cultured in ASF104 medium (AGF) containing HAT with aminopterine and 10% fetal calf serum. Then the medium was changed to HT medium without aminopterine, and cultured to select the hybridoma prepared by the fusion of the lymphocytes and the myeloma cells. The number of obtained clones was 169.

<3-2> Screening of Hybridomas

Hybridomas which produce anti-human CETP monoclonal antibody were screened by the CETP activity assay system established in Example 1.

The purified human CETP prepared in Example 2 and each culture supernatant of the hybridoma obtaining(60 µl) were added to the mixture of the donor lipoprotein prepared in Example<1-1>([$^3$H]CE-HDL$_3$ containing 0.21 µg of cholesterol) and the acceptor lipoprotein prepared in Example<1-2>(LDL containing 21 µg of cholesterol). Then, TBS was added to prepare the total volume of 600 µl/tube.

The prepared solution was treated similarly to the procedure described in Example<1-3>. The activity of CETP was determined for each sample. Then, by comparing it with the activity of a control sample, CETP inhibition activity (inhibition activity against CE-transporting activity of CETP) in the culture supernatant of the hybridoma was determined. By this screening, three positive clones, #72-1, #86-2, and #176-1, which have different CETP inhibition activities were obtained.

Two hybridomas, #72-1 and #86-2 were deposited in the National Institute of Bioscience and Human-Technology Agency of Industrial Science and Technology on Dec. 20, 1994 (1-1-3, Higashi, Tsukuba, Ibaraki, Japan). Their International accession numbers are FERM BP-4944 and FERM BP-4945, respectively.

<3-3> Large Scale Preparation of Monoclonal Antibodies

Each of the hybridomas #72-1, #86-2, or #176-1($10^6$ to $10^7$ cells/0.5 ml/Mouse) were administrated to 15 of ICR nude mice(female, 7–8 week age, purchased from Charles River) intraperitoneally. Ten days after, ascites were collected from the mice anesthetized according to a known method. Then, monoclonal antibodies were prepared in large scale from the ascites.

<3-4> Isotyping

Isotyping for the monoclonal antibodies #72-1, #86-2 and #176-1, was performed with a Mouse monoclonal antibody isotyping kit(Amersham) according to the protocol provided with the kit. The result showed that both #72-1 and #86-2 were IgG1, and #176-1 was IgG2b.

<3-5> Purification of the Monoclonal Antibody

Five ml of each of the monoclonal antibodies #72-1, #86-2, and #176-1, prepared as supernatants, were diluted three-fold with 0.06 M acetate buffer(pH 4.0), and pH was adjusted to 4.8 with 1 N HCl. Then, 16.5 µl of caprylic acid(Wako Pure Chemical) was gradually added to the diluted solution at room temperature to react for 30 minutes. After that, the mixture was centrifuged at 10,000 rpm for 20 minutes to precipitate proteins except antibodies. Supernatants were collected, and filtered(Millipore) to remove white precipitates. Filtrates were dialyzed against phosphate buffer for 2 hr.

After dialysis, ammonium sulfate(26.2 g/100 ml) was added little by little with stirring to react at 4° C. for 120 minutes. Then, the mixture was centrifuged at 10,000 rpm for 20 minutes to collect precipitates. Phosphate buffer was added to the precipitate, and dialyzed against the phosphate buffer at 4° C. for 24 hr, and then the purified monoclonal antibodies #72-1, #86-2, and #176-1, respectively were obtained.

Example 4

Purification of Human CETP by Affinity Chromatography

The purified human CETP prepared in Example 2 was further purified by affinity column chromatography in which the monoclonal antibody #72-1 was used and then was characterized.

<4-1> Preparation of Immobilized Monoclonal Antibody (as an adsorbent medium in a column)

HITRAP-NHS-ACTIVATED SEPHAROSE HP column(1 ml, Pharmacia Biotech) was employed, and the experiment was performed according to the manufacturer's protocol. The monoclonal antibody #72-1 was dissolved in 0.2 M sodium hydrogen carbonate(pH 8.3) containing 0.5 M NaCl and was injected into the column at a ratio of 5 mg/ml. Then, the monoclonal antibody was reacted with the column for 45 minutes to immobilize the antibody onto NHS-ACTIVATED SEPHAROSE to prepare the immobilized monoclonal antibody #72-1.

<4-2> Purification by affinity chromatography

Figure 3:
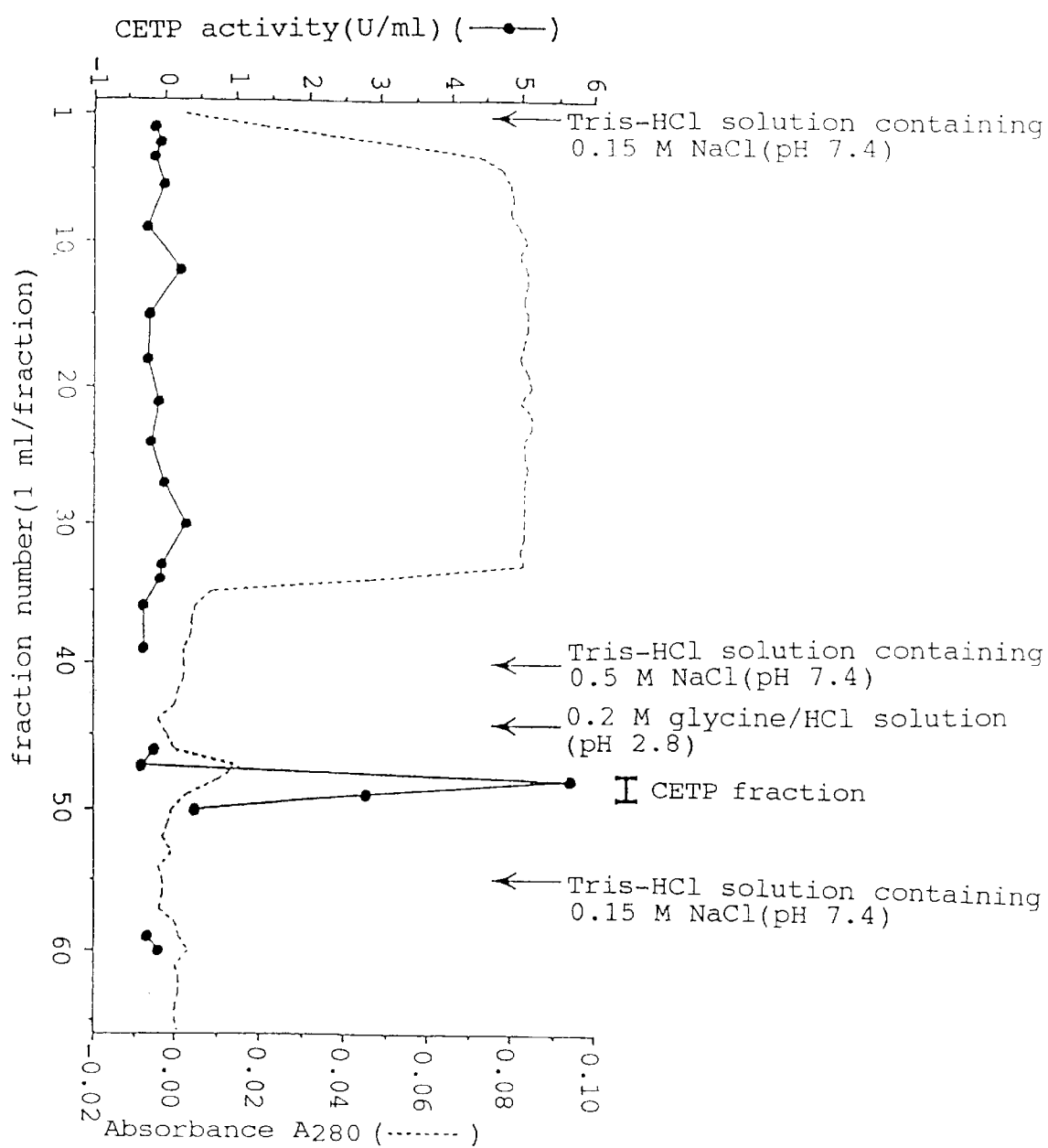
FIG. 3 shows a chromatogram of human CETP by affinity column chromatography using the monoclonal antibody #72-1.

A solution containing the purified human CETP obtained in Example 2 was applied on the column prepared in Example<4-1>. Then, the column was washed with 5 ml of 50 mM Tris-HCl buffer(pH 7.6) containing 500 mM NaCl, and eluted with 2 mM glycine-HCl(pH 2.8). The eluted fraction was neutralized with 2 M Tris-HCl(pH 8.8). The elution profile was monitored by measuring the absorbance at 280 nm. The result is shown in FIG. 3. Based on the elution profile, active fractions containing human CETP were pooled. The pooled fraction were dialyzed against 50 mM Tris-HCl containing 0.15 M NaCl(pH 7.6), and a highly purified human CETP was prepared.

<4-3> Characterization of Purified Human CETP

As described in FIG. 3, enzyme activity(specific activity) of the purified CETP obtained in Example 4 was 1,100 U/mg.

The molecular weight of the purified human CETP was analyzed by using SDS-PAGE(sodium dodecyl sulfate polyacrylamide gel electrophoresis).

Figure 4:
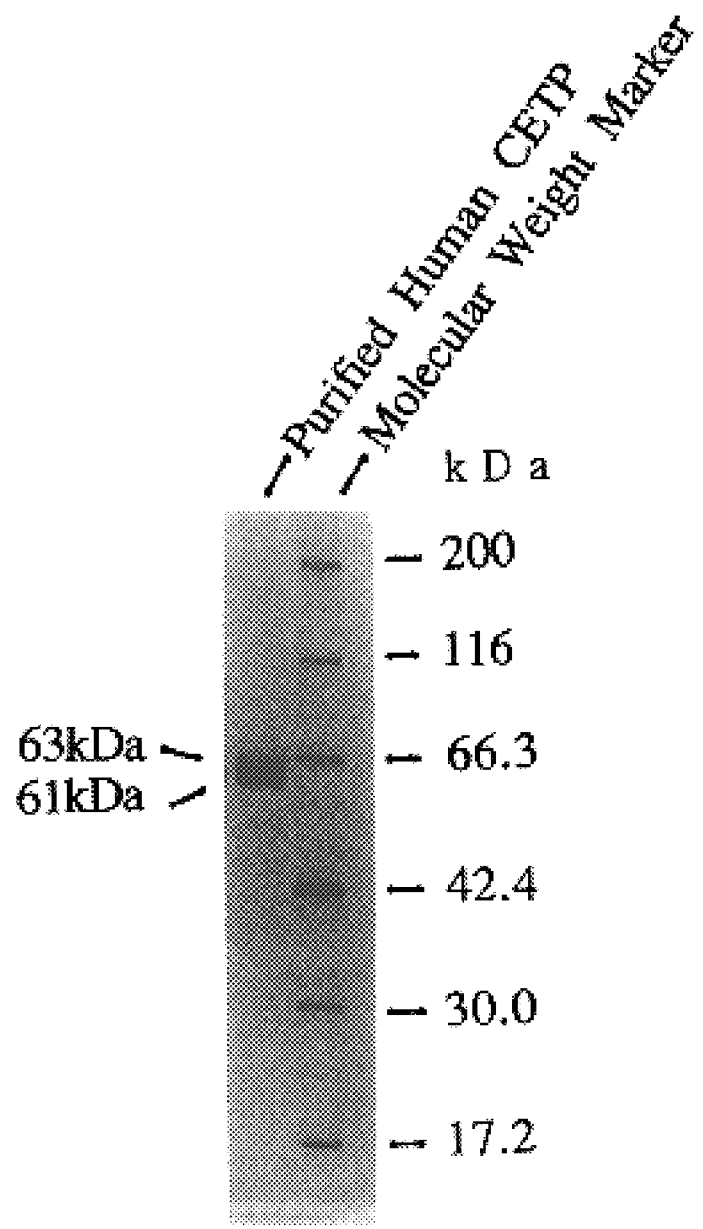
FIG. 4 shows a electrophoresis of human CETP purified by the affinity column chromatography by using the monoclonal antibody #72-1 showing a molecular weight.

The result is shown in FIG. 4.

It was confirmed that the purified human CETP obtained in the present Example comprises two proteins of about 63,000 Da and 61,000 Da. Many researchers tried to purify human CETP, and the values of the molecular weight were reported. Such values reported were not identical to each other because the purification method, purity of the protein and/or analysis of the molecular weight were different. However, they were in the range of about 64,000 to 66,000 Da. Compared to such values, it was demonstrated that the purity of the CETP obtained in Example 4 was very high.

Example 5

Characterization of Anti-human CETP Monoclonal Antibody

<5-1> Reactivity to Human CETP

The reactivity of each of the purified monoclonal antibodies #72-1, #86-2, and #176-1, prepared in Example 3 was confirmed by determining human CETP-transporting activity assayed by the CETP activity assay system established in Example 1, in the same manner as in Example<3-2>.

The purified human CETP prepared in Example 4, and 20 µl of each of the purified monoclonal antibodies, #72-1, #86-2, and #176-1, which were diluted at various concentrations with Tris-HCl buffer(pH 7.4) containing 0.15 M NaCl were added to the mixture of the donor lipoprotein ([$^3$H]CE-HDL$_3$ containing 0.21 g of cholesterol) prepared in Example<1-1> and the acceptor lipoprotein(LDL containing 21 µg of cholesterol) prepared in Example<1-2>. Then TBS was further added to bring the total volume to 600 µl/tube.

Figure 5:
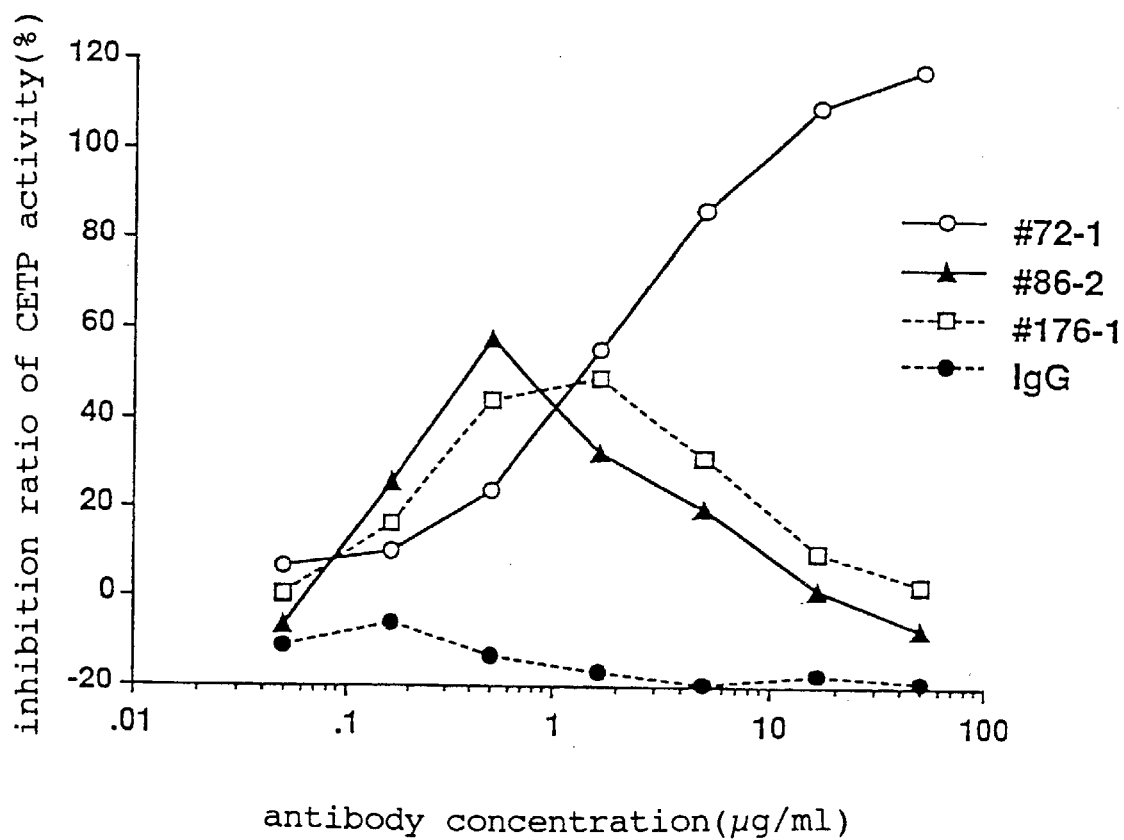
FIG. 5 shows the reactivity of the monoclonal antibodies, #72-1, #86-2, and #176-1 to purified human CETP.

The prepared solution was treated in a similar manner as in the procedure described in Example<1-3>. The CETP activity for each sample as well as for the control sample without the monoclonal antibody was determined. Comparing the values of the corresponding samples, the CETP inhibition activity for each monoclonal antibody was determined. As a reference, mouse IgG (sigma) was also used. The result is shown in FIG. 5.

The monolonal antibody #72-1 showed dose-dependent inhibition of the CE-transporting activity (human CETP activity) of the human CETP, particularly, the human CETP activity was inhibited by 100% at the concentration equal to or more than 10 µg/ml. In contrast, the monoclonal antibody #86-2 did not show dose-dependent inhibition. This monoclonal antibody showed the maximum inhibition(58%) at the concentration of about 0.5 µg/ml; however, it did not show any inhibition at the concentration equal to or more than 17 µg/ml. The monoclonal antibody #176-1 did not show dose-dependent CETP inhibition activity, neither did #86-2, and it showed the maximum inhibition(50%) occurring at the concentration of about 1.0 µg/ml.

Based on the above results, it was demonstrated that there is a high possibility that the epitope recognized by the monoclonal antibody #72-1 is different from that recognized by the other monoclonal antibodies #86-2 and #176-1.

<5-2> Reactivity with Rabbit CETP

The respective reactivity of the monoclonal antibodies #72-1, #86-2 and #176-1 prepared in Example 3 for the rabbit CETP was confirmed by the CETP activity assay system in a similar manner as in Example 1. The purified rabbit CETP, the donor lipoprotein and the acceptor lipoprotein used for the assay system were prepared as described below.

<5-2-1> Preparation of Purified Rabbit CETP

The following procedure was performed according to a known method at 4° C. or in an ice bath.

(1) Dextran Sulfate Treatment

Peripheral blood was obtained from plural rabbits(Japan white, Kitayama rabes). The blood was centrifuged to remove red blood cells according to the conventional method, and one hundred ml of rabbit plasma was obtained. Two hundred ml of distilled water, 10 ml of 10% of dextran sulfate(molecular weight 500,000 Da) and 7.9 ml of 4 M CaCl$_2$ were added to the 100 ml of the plasma obtained, and the mixture was gently stirred in an ice bath for 15 minutes. The mixture was then centrifuged at 20,000×g for 20 hr at 4° C. to fractionate the insoluble dextran sulfate/lipoprotein complex, and then the supernatants were collected.

(2) Purification by PHENYL SEPHAROSE Column Chromatography

Three molar NaCl, 0.01% NaN$_3$, 0 µg/ml of gentamycin sulfate and 0.05% EDTA were added to the supernatant obtained in the above (1), and adjusted to pH 7.4. Prior to applying the above mixture, a HILOAD 26/10(PHENYL SEPHAROSE column, Pharmacia Biotech) was equilibrated with the same solution described above. Then, the mixture was applied on the column, and washed with 0.15 M NaCl solution(pH 7.4) containing 0.01% NaN$_3$, gentamycin sulfate (50 µg/ml) and 0.05% EDTA. After that, adsorbed components were eluted by using the solution without NaCl, and 20% ethanol. The elution profile was monitored by measuring the absorbance at 280 nm.

Figure 6:
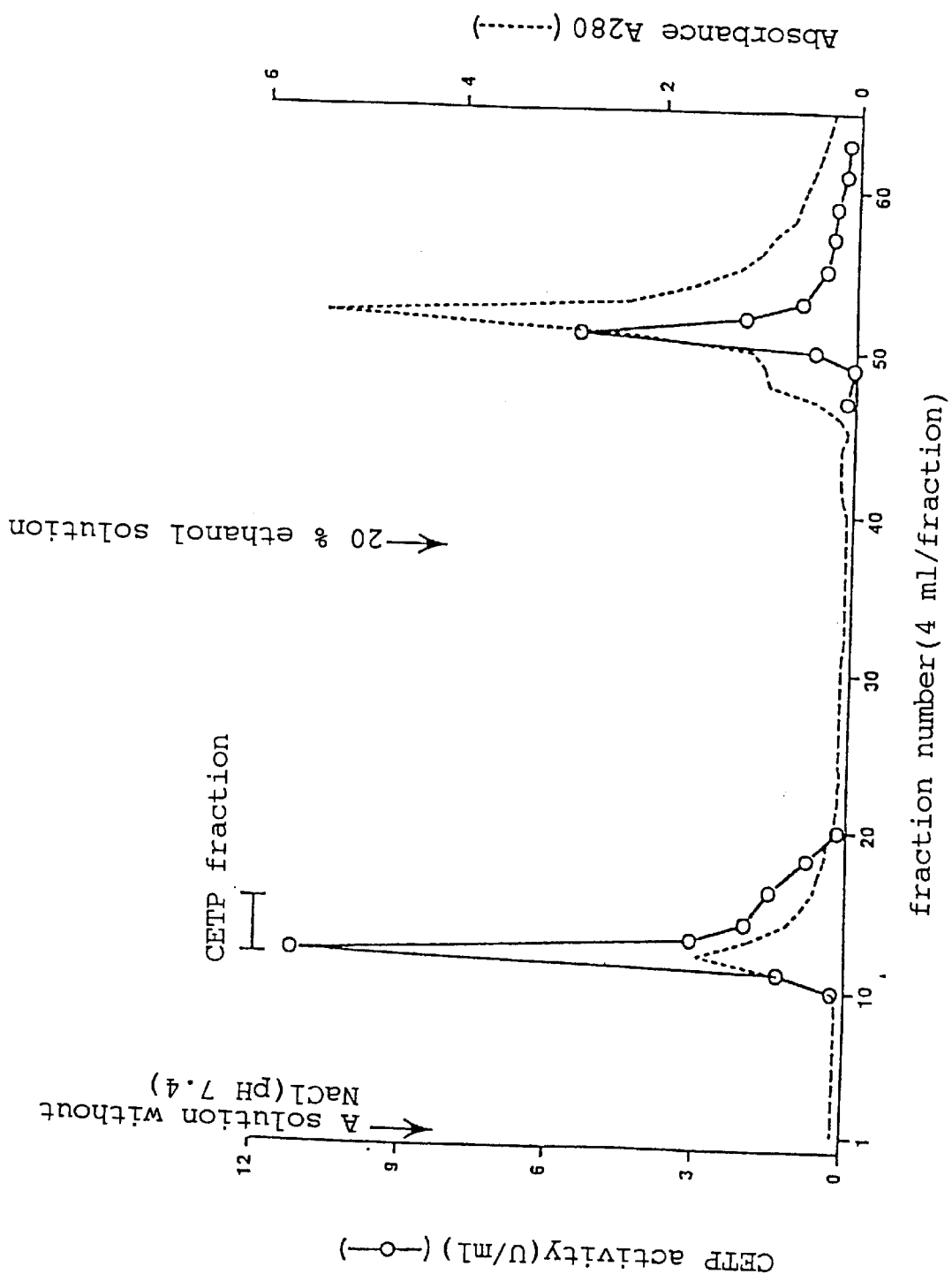
FIG. 6 shows a chromatogram of rabbit CETP by PHENYL SEPHAROSE column chromatography.

The result is shown in FIG. 6. Based on the elution profile, the active fractions containing rabbit CETP were pooled.

(3) Purification by BLUE SEPHAROSE Column Chromatography

The active fractions obtained in the above (2) were dialyzed against 50 mM HEPES buffer(N-2 hydroxyethylpiperadine-N'-2-ethanesulfonic acid)(pH 7.0). Then, the dialyzed sample was applied to a BLUE SEPHAROSE column(CL-6B, 1.5×8.5 cm, Pharmacia Biotech) which was equilibrated with the buffer. The column was washed with the buffer, and then eluted with the solution comprising 1.5 M NaCl and the buffer(pH 7.0). The elution profile was monitored by measuring the absorbance at 280 nm.

Figure 7:
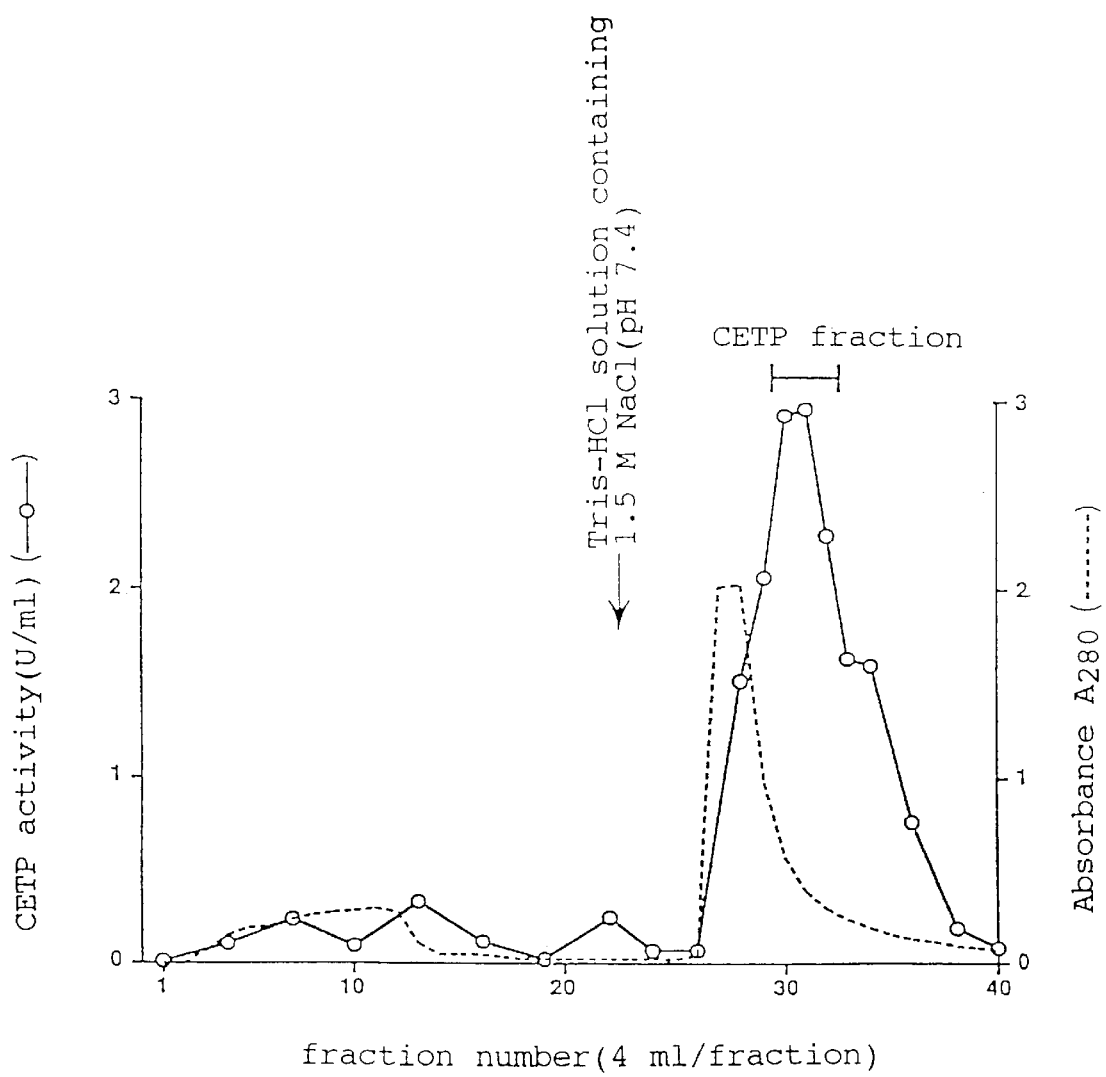
FIG. 7 shows a chromatogram of rabbit CETP by BLUE SEPHAROSE column chromatography.

The result is shown in FIG. 7. Based on the elution profile, the active fractions containing rabbit CETP were pooled.

(4) Purification by Succinylated LDL SEPHAROSE Column Chromatography

The active fraction obtained in the above step (3) was dialyzed against the solution comprising 60 mM Nacl containing 0.025% EDTA, and 50 mM HEPES buffer(pH 7.4). Then, a succinylated LDL SEPHAROSE column was prepared by adding succinylated LDL to CNBr-ACTIVATED SEPHAROSE 4B (1.5×8.5 cm, Pharmacia Biotech). The column was equilibrated with 39 mM phosphate buffer (pH 7.4) and 60 mM NaCl(pH 7.4) containing 0.025%. Then, the dialyzed sample was applied to the column. The column was washed with the same buffer, and then eluted with the solution(pH 7.4) containing 0.01% EDTA. The elution profile was monitored by measuring the absorbance at 280 nm.

Figure 8:
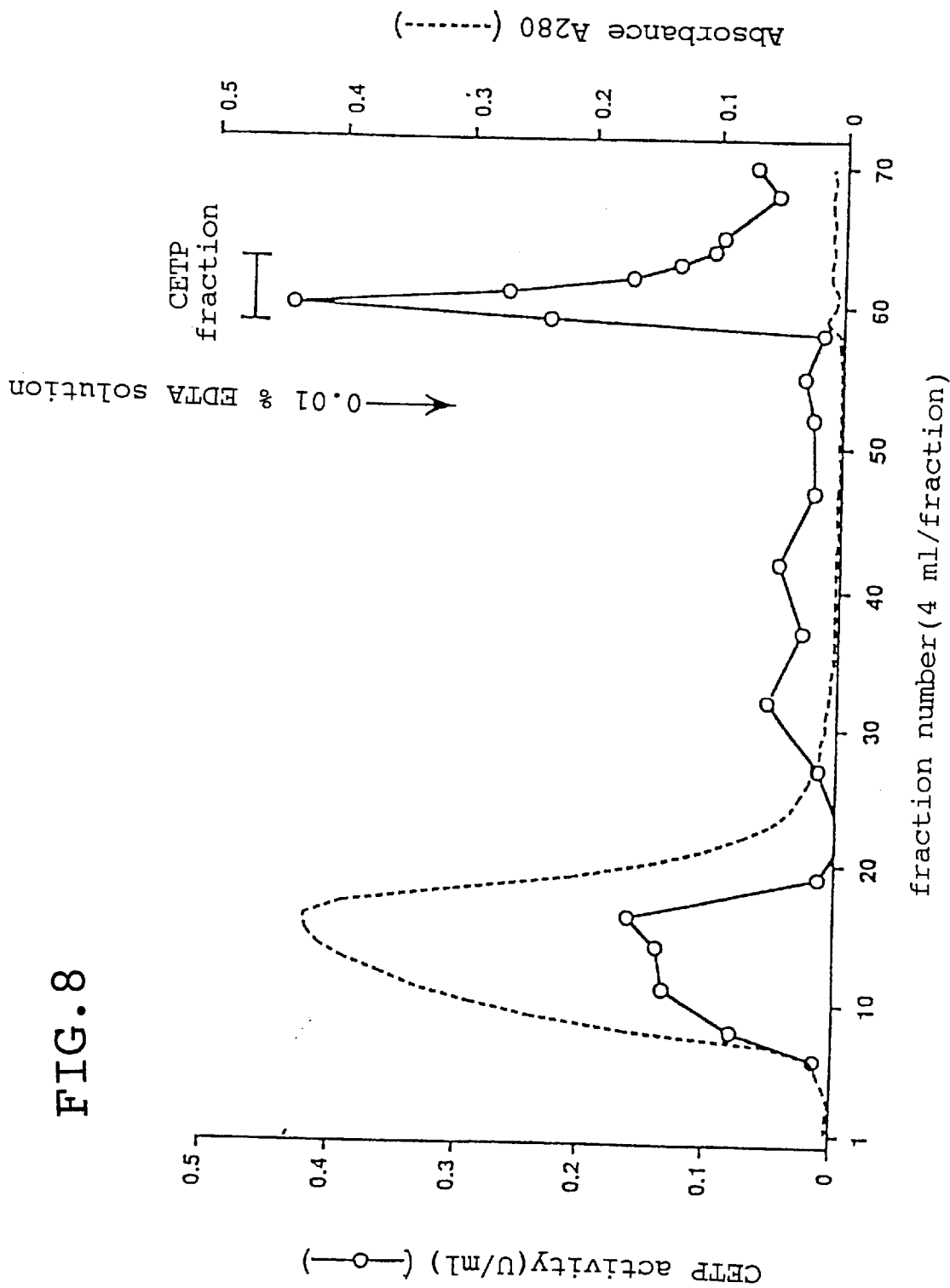
FIG. 8 shows a chromatogram of rabbit CETP by succinylated LDL sepharose column chromatography.

The result is shown in FIG. 8. Based on the elution profile, the active fractions containing rabbit CETP were pooled to obtain the purified rabbit CETP.

m<5-2-2> The donor lipoprotein and the acceptor lipoprotein

According to a method similar to that described in both Example<1-1> and <1-2>, both the donor lipoprotein([$^3$H] CE-HDL$_3$ containing 0.21 μg cholesterol) and the acceptor lipoprotein(LDL containing 21 μg of cholesterol) were prepared by using rabbit plasma.

<5-2-3> Confirmation of the reactivity to rabbit CETP

The respective reactivity of the monoclonal antibodies #72-1, #86-2 and #176-1 with the rabbit CETP was confirmed by the CETP activity assay system in which purified rabbit CETP prepared in <5-2-1>, and the donor lipoprotein prepared and the acceptor lipoprotein prepared in <5-2-2> were used in the same manner as in Example <5-1>.

Figure 9:
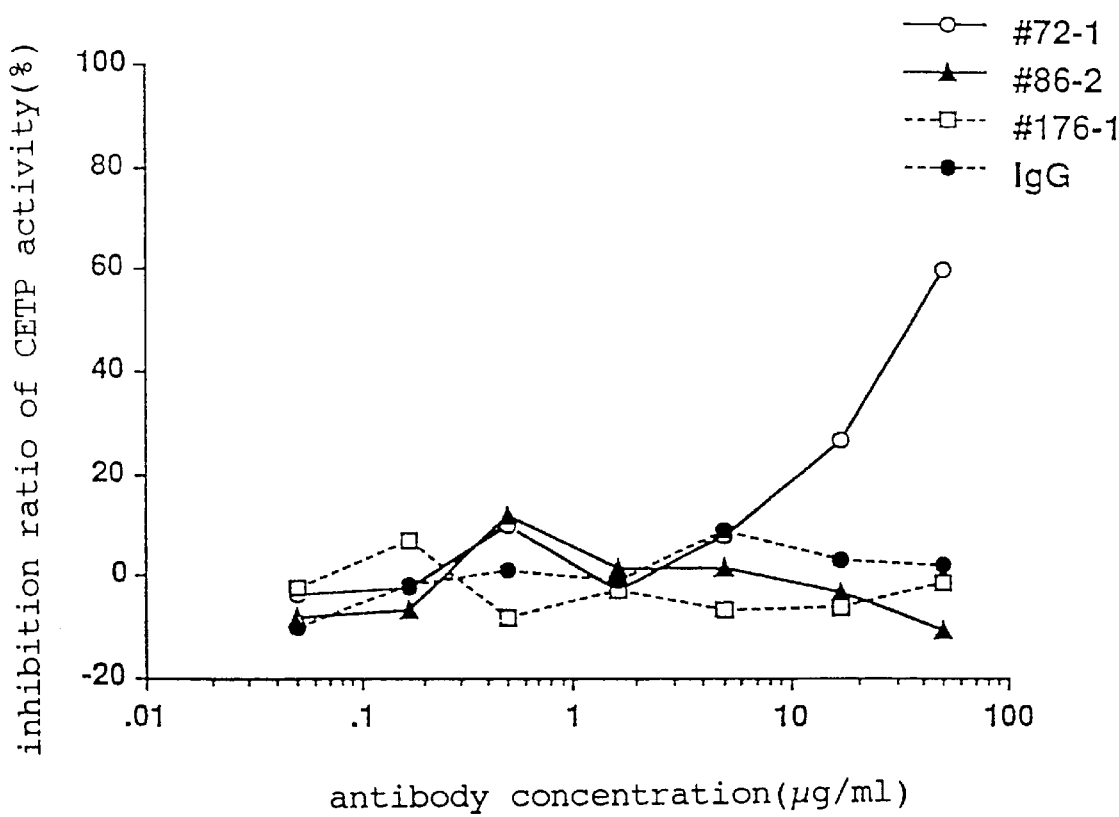
FIG. 9 shows the reactivity of the monoclonal antibodies, #72-1, #86-2, and #176-1 to purified rabbit CETP.

The result is shown in FIG. 9. Neither monoclonal antibody #86-2 nor #176-1 inhibited CE transport activity of rabbit CETP independent of concentration. Accordingly, these monoclonal antibodies did not have any specific reactivity with rabbit CETP. Furthermore, the monoclonal antibody #72-1 did not show any detectable reactivity with rabbit CETP at the concentration equal to or less than about 3 μg/ml.

Example 6

Preparation of Antibody Fragments, F(ab')$_2$ and Fab

The F(ab')$_2$ and Fab of the purified monoclonal antibodies prepared in Example 3, #72-1, #86-2, and #176-1, were prepared as follows.

Each of the monoclonal antibodies (5 mg/ml respectively) was added to 20 mM acetate buffer(pH 3.5), and incubated for 30 minutes at 37° C. Then, one ml of insolubilized pepsin(Pierce) was added to the incubated solution, and the mixture was further incubated for 12 hr at 37° C. while being rotated by a rotator. After that, the reaction mixture was centrifuged at 3,000 rpm for 10 minutes at 4° C. to collect the supernatants as the first supernatant.

The supernatant was subjected to Protein A affinity chromatography using a Protein A column kit(Amersham), and the procedure was performed according to the manufacturer's protocol. A binding buffer was added to the precipitate for suspension, and then the suspension was centrifuged at 3,000 rpm for 10 minutes at 4° C. to collect the supernatants as the second supernatant. Both the first and second supernatant were pooled, and the same amount of the binding buffer was added. Then, 1 N sodium hydroxide was added to adjust to pH 8.9. A Protein A SEPHAROSE column was equilibrated with the binding buffer prior to applying the mixture. The column was washed twice with 5 ml of the binding buffer, and then the eluted fractions were obtained. The eluted fractions were dialyzed against 2 L of 5 mM phosphate buffer (pH 6.8) for 24 hr at 4° C.

For further purification, the dialyzed sample was subjected to HPLC by using a hydroxylapatite column(Bio Rad). The dialyzed sample was applied onto the hydroxylapatite column. Then, the column was washed with 5 mM phosphate buffer for 15 minutes. Components retained on the column were subsequently eluted with a gradient elution buffer of 5 mM to 0.4 M phosphate buffer. The eluents were fractionated by using a fraction collector. The elution profile was monitored by measuring the absorbance at 280 nm to obtain fractions which contain F(ab')$_2$. The pooled fractions were dialyzed against 2 L of phosphate buffer at 4° C. for 24 hr to obtain the respective F(ab')$_2$ of the monoclonal antibodies#72-1, #86-2 and #176-1.

Example 7

Establishment of Human CETP Assay Method Using Sandwich ELISA

<7-1> Preparation of the Solid Phase with Immobilized Monoclonal Antibody

Each of the purified monoclonal antibodies #72-1, #86-2 and #176-1 prepared in Example 3 was diluted with phosphate buffer(pH 7.4) so as to be 10 ng/well to 1 μg/well. Fifty μl of each diluted antibody solution was added into wells of 96 well microtiter plates for ELISA(Corning). The plates with the solutions were incubated at 4° C. for 24 hr to adsorb each monoclonal antibody onto the inside of the well. Then each well was washed four times with 300 μl of phosphate solution containing 0.1% TWEEN 20. After discarding the phosphate buffer, 300 μl of a blocking agent, BLOCK ACE(Dainippon Pharmaceutical), was added to the well and left standing for 2 hrs. at room temperature to block the sites not bound by the antibody. Each well was washed four times with 300 μl of phosphate solution containing 0.1% TWEEN 20.

<7-2> Preparation of labeled Monoclonal Antibodies

One mg/ml of each of the solutions of the purified monoclonal antibody #72-1, #86-2 and #176-1, prepared in Example 3, were dialyzed against 0.1 M NaHCO$_3$(pH 8.2 to 8.3) at 4° C. for 24 hr. Then, one hundred μl of NHS-biotin(2 mg/ml, Funakoshi) was added to the dialyzed antibody solution, and stirred vigorously. The antibody solution was incubated for 4 hr at room temperature. After that the antibody solution was dialyzed against phosphate buffer at 4° C. for 24 hr.

<7-3> Establishment of the Assay Method by Using Sandwich ELISA

An exemplary The human CETP assay method by sandwich ELISA of the present invention is as follows.

Each of the monoclonal antibodies #72-1, #86-2, and #176-1 was immobilized respectively onto microplates at the concentration of 10 ng/well to 1 μg/well as described in <7-1>. The above-mentioned microplates so prepared are referred to as the immobilized microplate. The immobilized plates were washed three times with phosphate buffer containing 0.1% TWEEN 20. Phosphate buffer containing 10% BLOCK ACE (Dainippon Pharm-) was used for diluting the samples which were the purified human CETP standard prepared in Example <4-2>, the lipoprotein-removed plasma of healthy volunteers prepared in Example <2-1>, or the plasma of various patients prepared in the same manner described in Example <2-1>. The immobilized plates with 100 μl of the diluted samples were incubated at room temperature for 1 hr. The plates were washed three times with the phosphate buffer containing 0.1% TWEEN 20 . The biotin-labeled monoclonal antibodies #72-1, #86-2, or #176-1, prepared in Example <7-2>, were diluted with the phosphate buffer containing 10% BLOCK ACE to 3 ng/well to 1 µg/well. Then, the plates to which 50 µl of the biotin labeled monoclonal antibody were added were incubated at room temperature for 1 hr. After that, the immobilized microplates were washed three times with the phosphate buffer containing 0.1% TWEEN 20. Fifty µl of streptavidin-β-galactosidase(Gibco BRL) diluted 1,000 times with the a solution comprising 20 mM HEPES and 0.5 M NaCl(pH 7.0) containing bovine serum albumin (BSA, 1 mg/ml) were was added to each well of the immobilized plates. Then, the immobilized microplates were incubated at room temperature for 1 hr.

The immobilized microplates were washed three times with the phosphate buffer containing 0.1% TWEEN 20. After that, fifty µl of 0.015% or 0.01% of 4-methyl-umbelliferyl-β-D-galactoside(Sigma) diluted with 10 mM phosphate buffer containing 1 mg/ml of BSA, 100 mM NaCl, 1 mM $MgCl_2$(pH 7.0) were added to each well of the immobilized microplates. Then, the immobilized microplates were incubated at room temperature for 10 or 20 minutes. After that, one hundred µl of $Na_2CO_3$ solution was added to the wells to terminate the reaction. Fluorescence intensity of the wells was measured with a Fluoroscan II microplate fluorometer(Flow Laboratories) at an emission wavelength of 460 nm (355 nm for excitation). The amount of CETP in the sample was determined from the calibration curve obtained in the following Example.

Figure 10:
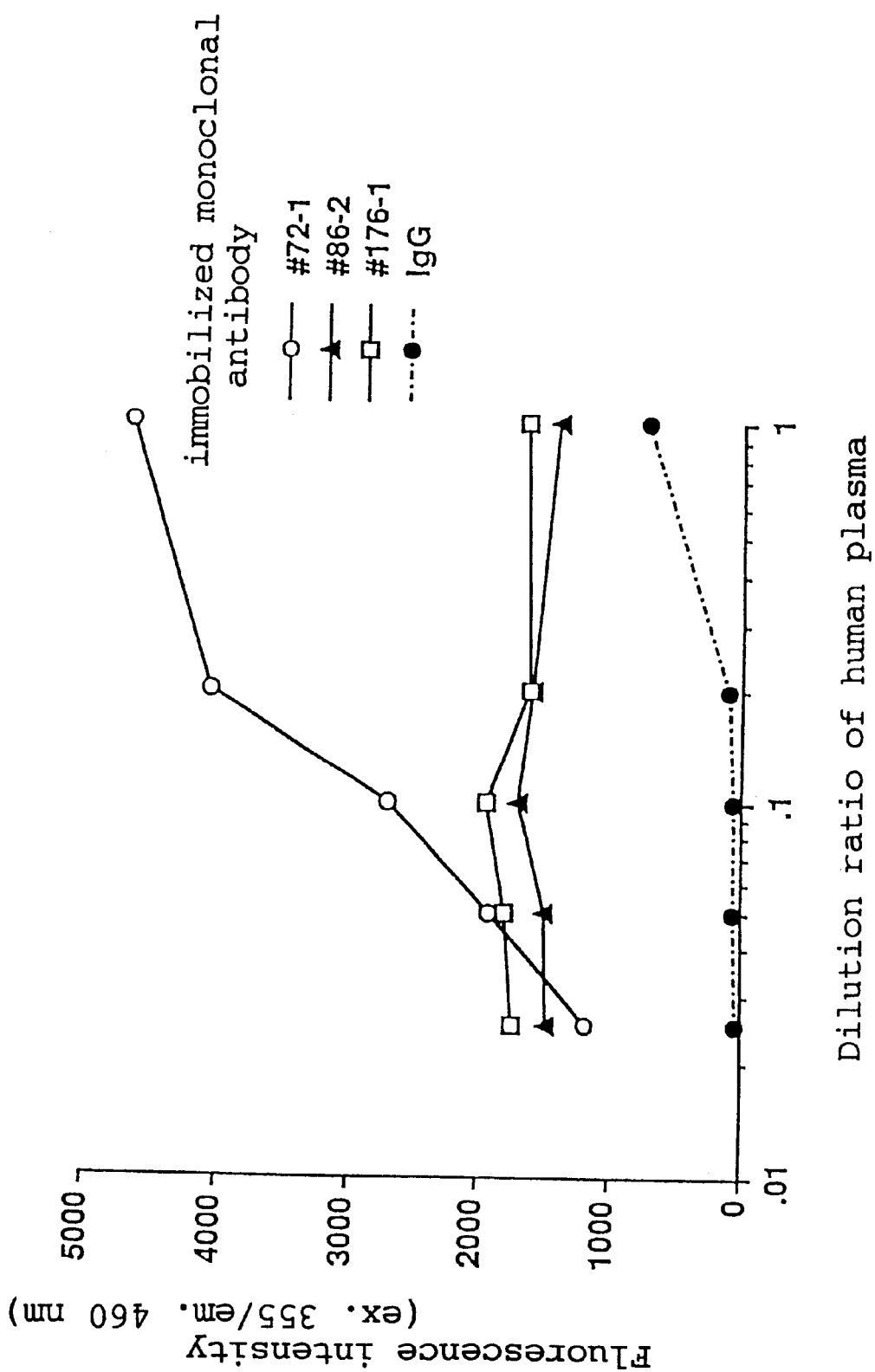
FIG. 10 shows the sensitivity of quantification when the labeled monoclonal antibody #86-2 and several immobilized antibodies are combined.
Figure 11:
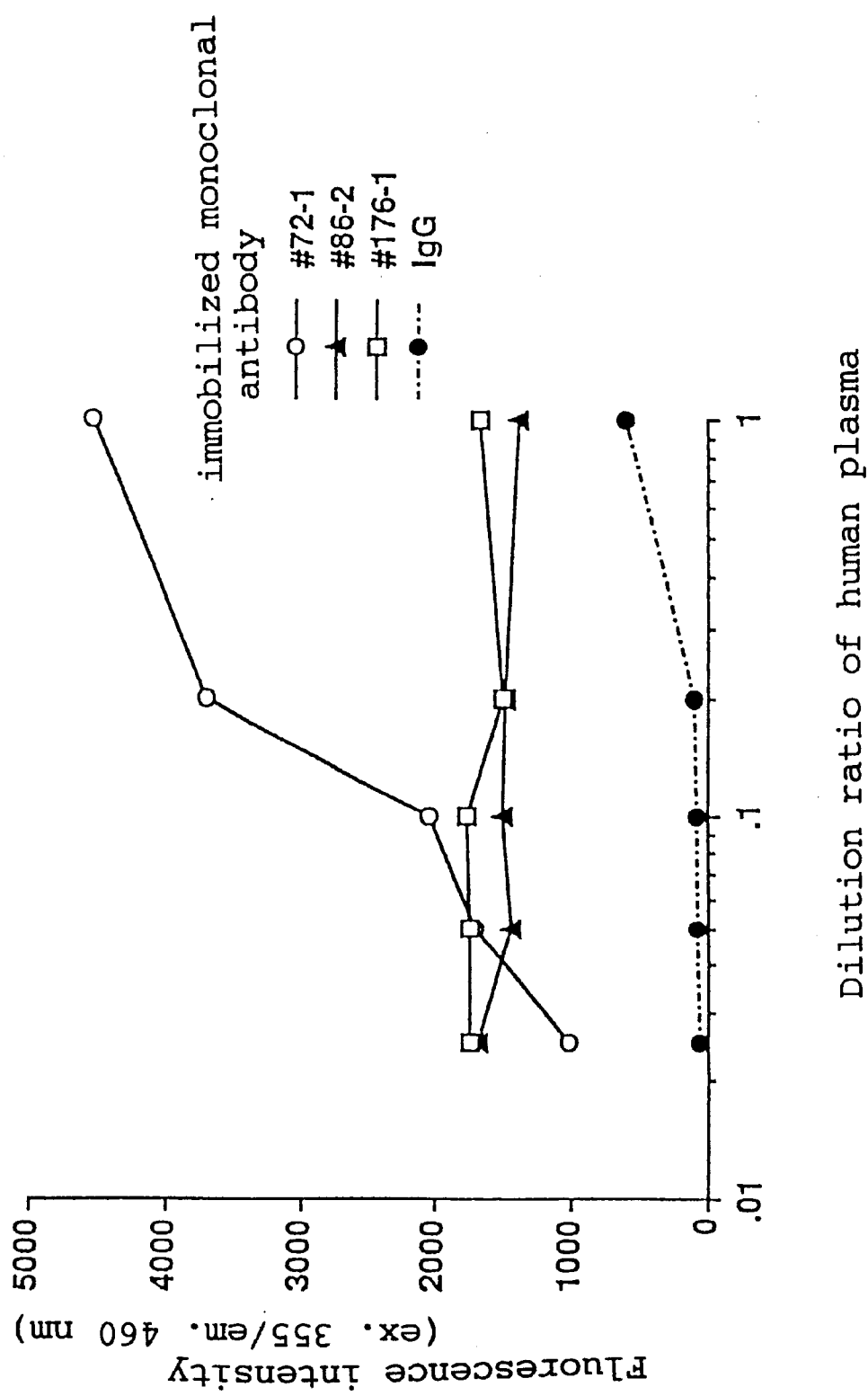
FIG. 11 shows the sensitivity of quantification when the labeled monoclonal antibody #176-1 and several immobilized antibodies are combined.
Figure 12:
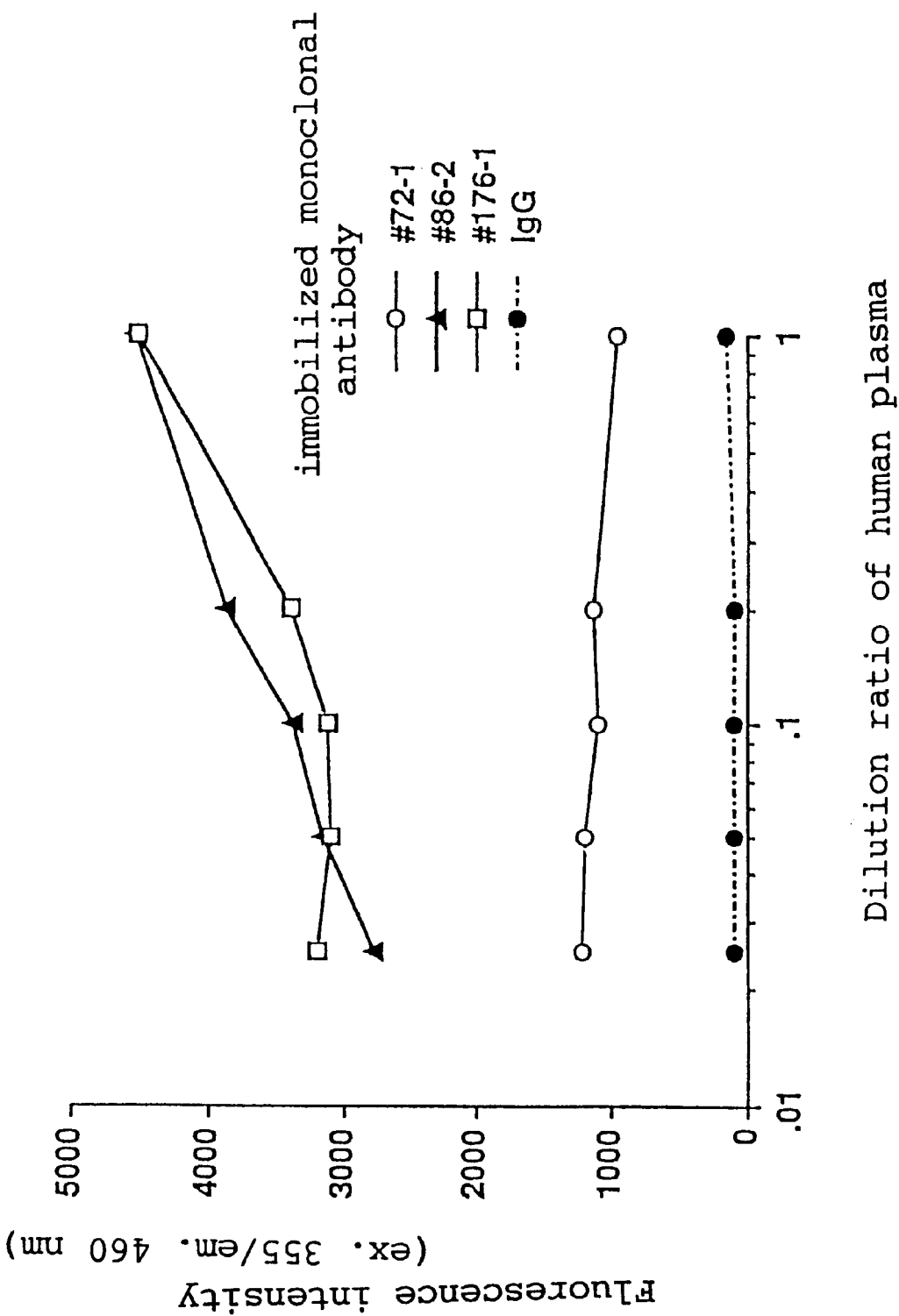
FIG. 12 shows the sensitivity of quantification when the labeled monoclonal antibody #72-1 and several immobilized antibodies are combined.
Figure 13:
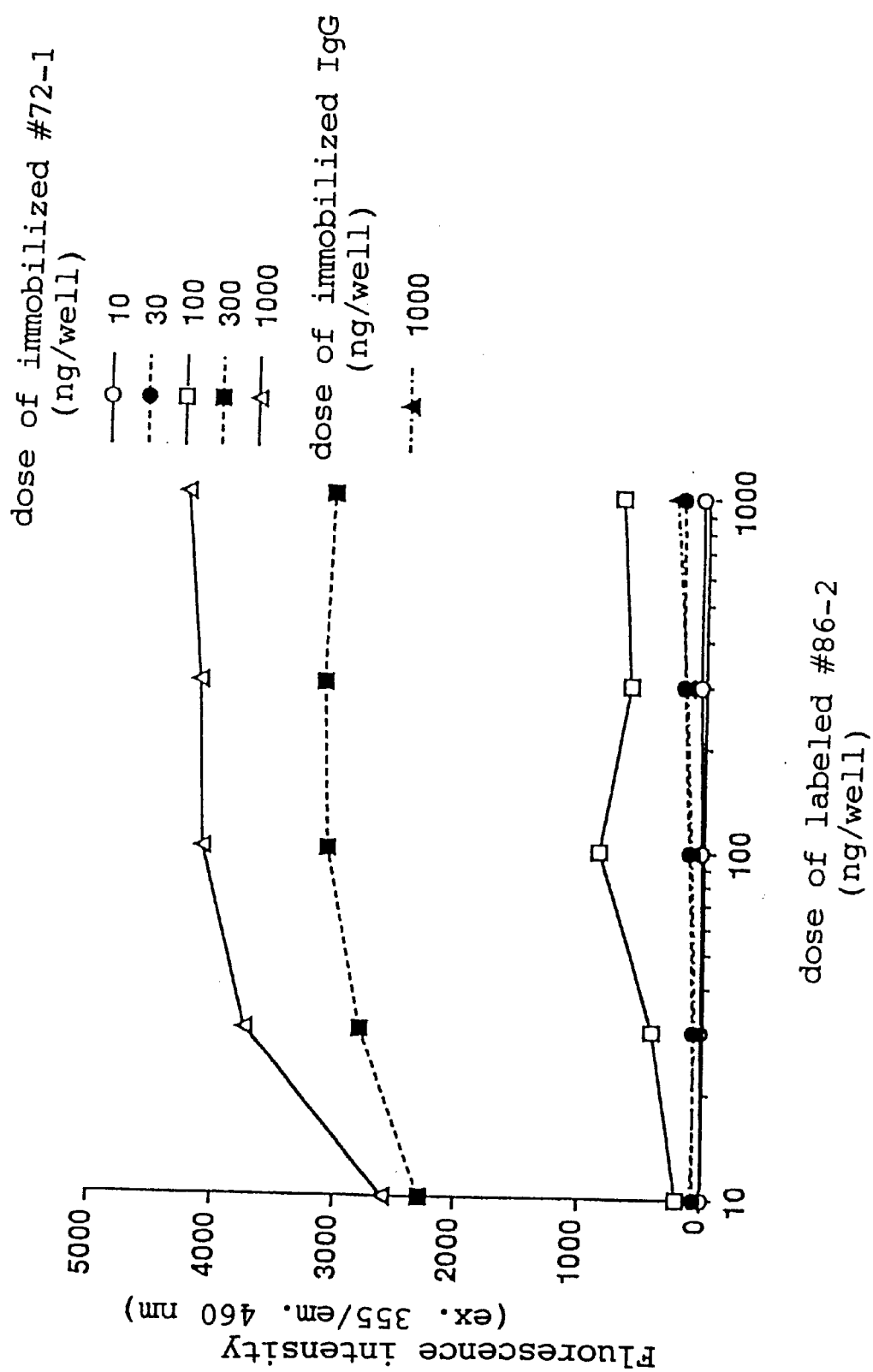
FIG. 13 shows the sensitivity of quantification when the labeled monoclonal antibody #86-2 and the immobilized antibody #72-1 at several concentration are combined.
Figure 14:
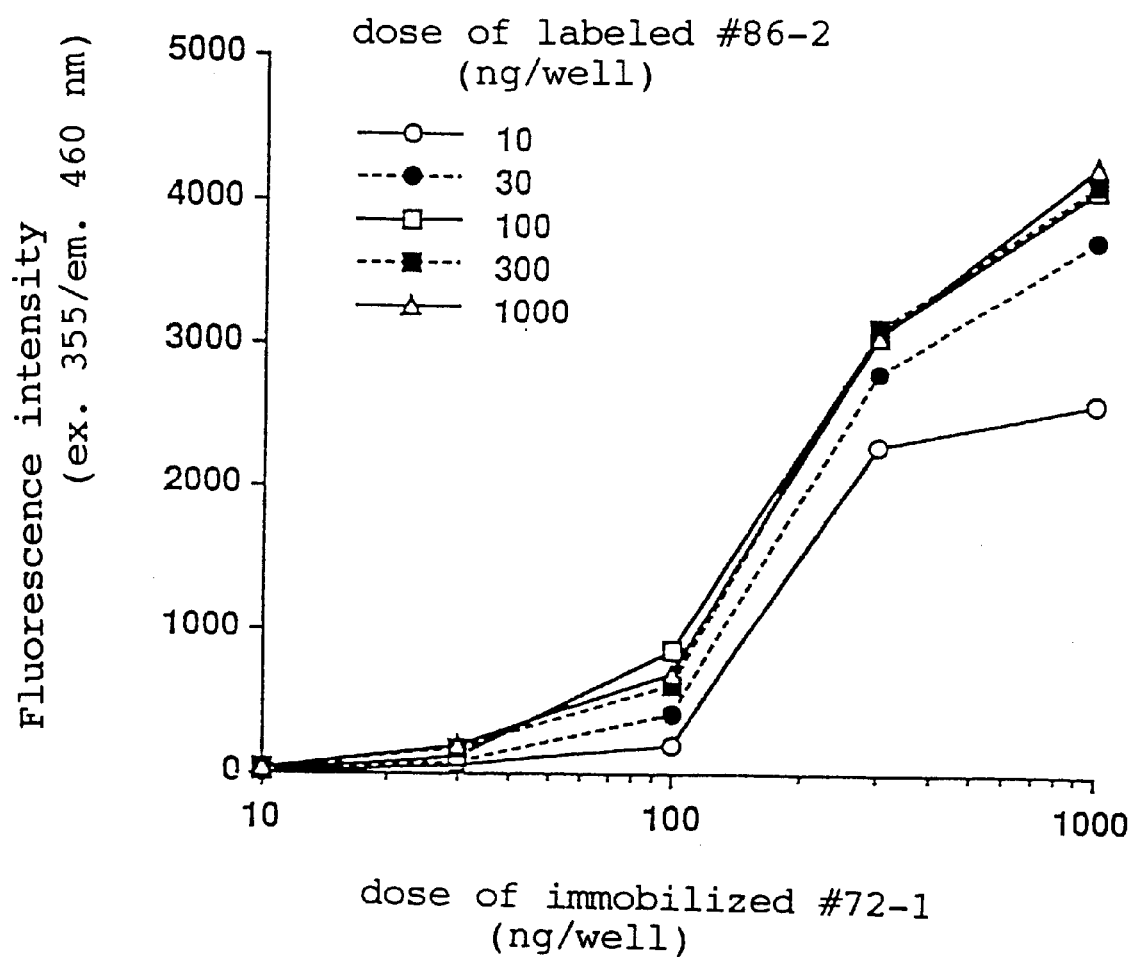
FIG. 14 shows the sensitivity of quantification when the labeled monoclonal antibody #72-1 and the immobilized antibody #86-2 at several concentration are combined.
Figure 15:
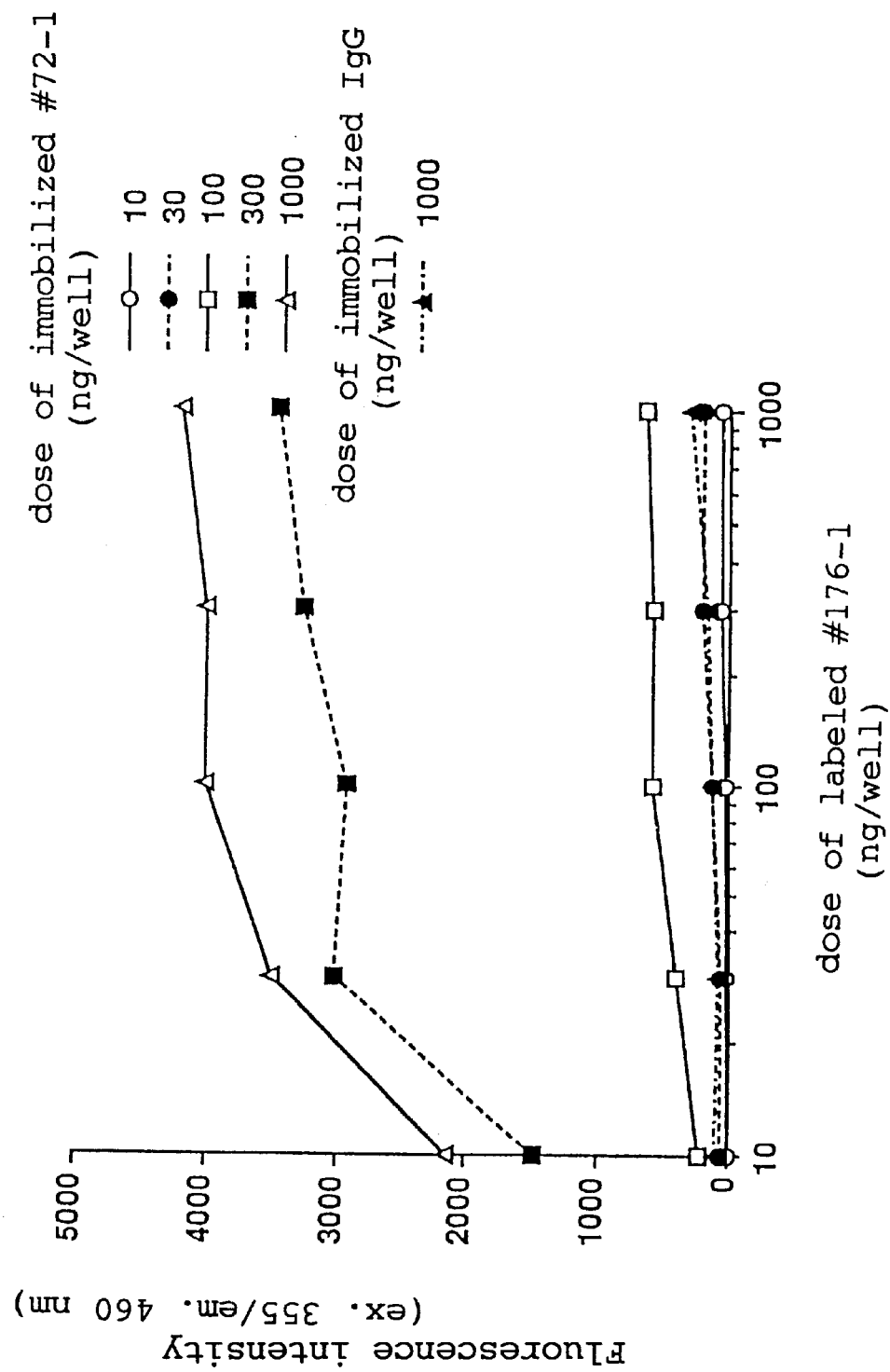
FIG. 15 shows the sensitivity of quantification when the labeled monoclonal antibody #176-1 and the immobilized antibody #72-1 at several concentration are combined.
Figure 16:
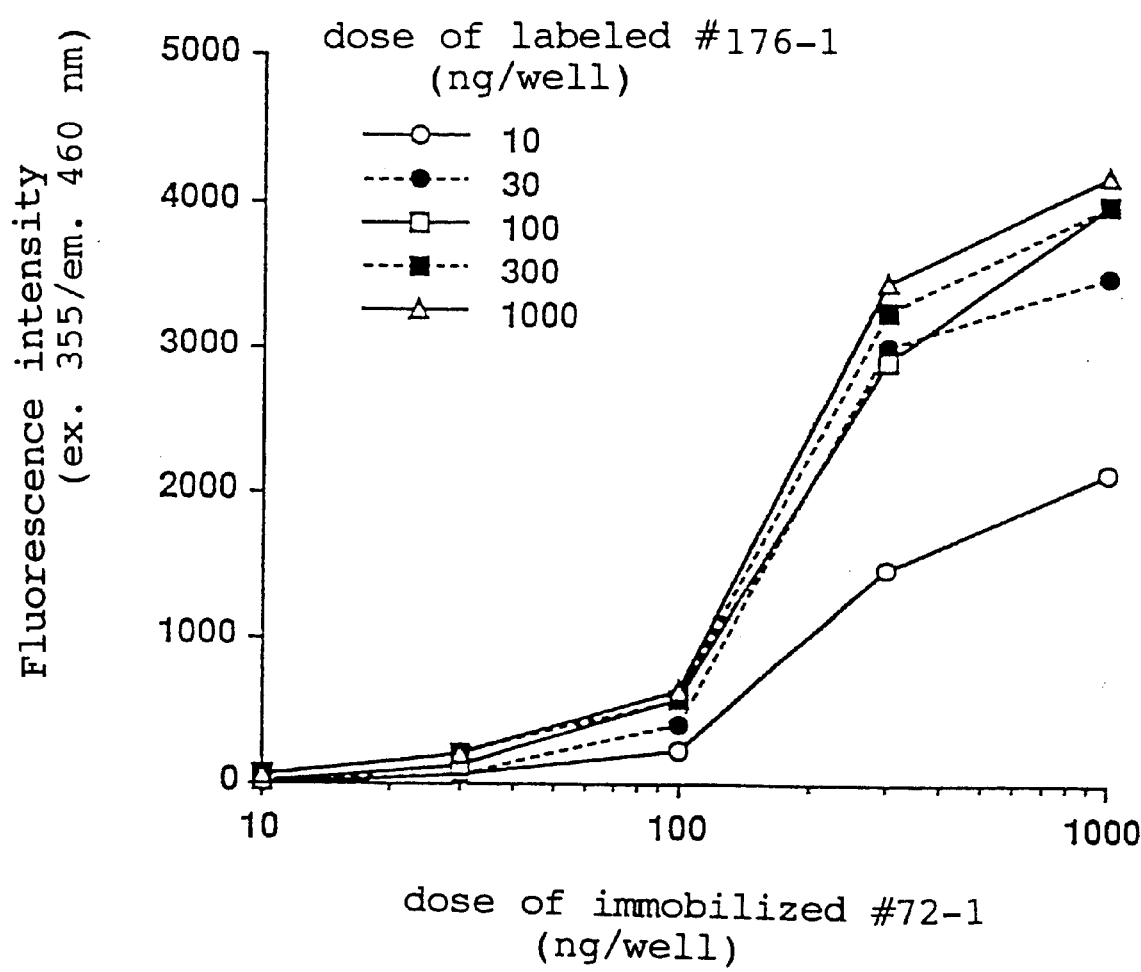
FIG. 16 shows the sensitivity of quantification when the labeled monoclonal antibody #72-1 and the immobilized antibody #176-1 at several concentration are combined.
Figure 17:
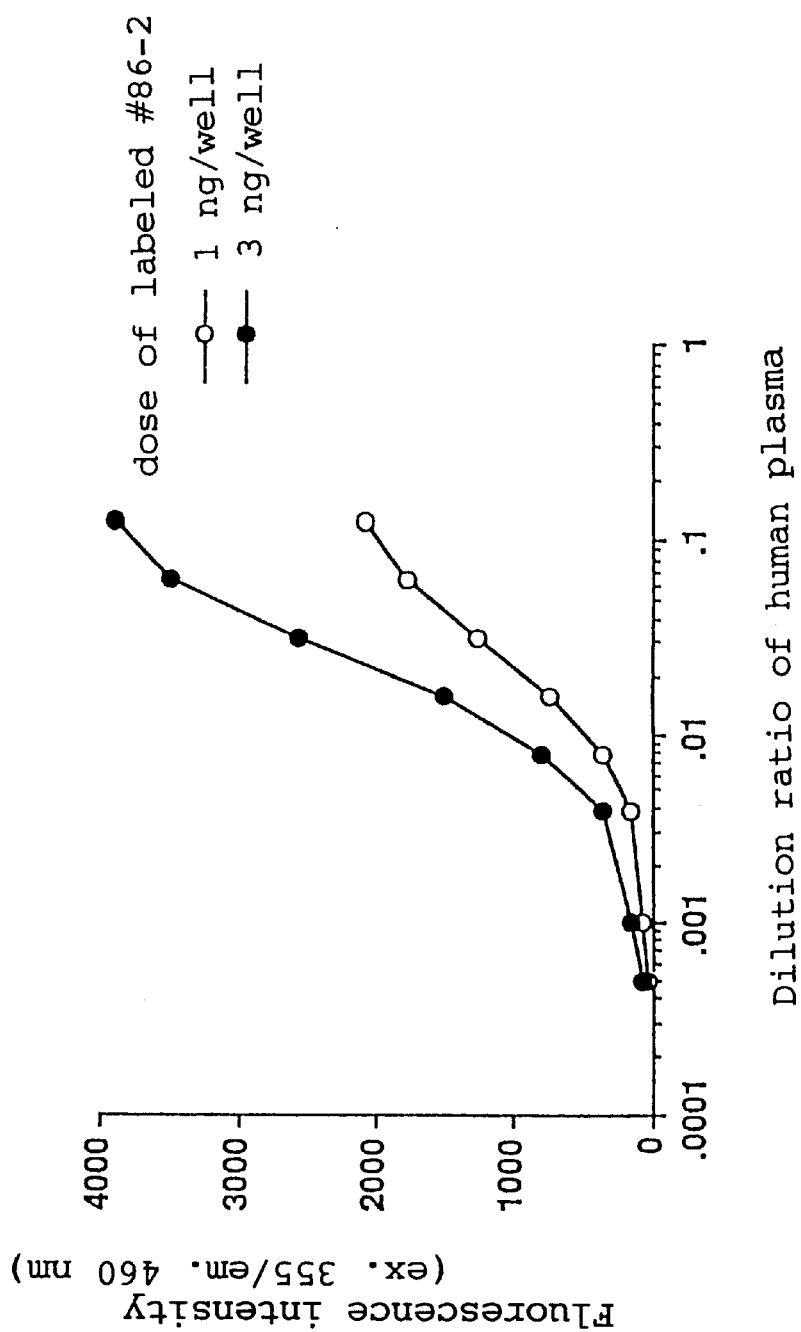
FIG. 17 shows the sensitivity of quantification when the labeled monoclonal antibody #72-1(1 $\mu$g/ml) and the immobilized antibody #86-2(1 ng/well or 3 ng/well) are combined.

The results of the assay when various combinations of the monoclonal antibodies(#72-1, #86-2, and #176-1) are immobilized or labeled are shown in FIGS. 10 to 12. As a result, it was confirmed that quantitative assay was achieved by using a combination of the different monoclonal antibodies #72-1, #86-2 and #176-1, immobilized or labeled, for example, #72-1 and #86-2, or #72-1 and #176-1.

The optimal concentration of the immobilized or the labeled monoclonal antibody was determined under the following conditions. As a substrate, 4-methyl-umbelliferyl-β-D-galactoside was used, and as an assay sample, the lipoprotein-removed plasma from the healthy volunteers prepared in Example <2-1> was used.

(1) the immobilized monoclonal antibody:
   #72-1(10 ng to 1 µg/well)
   the labeled monoclonal antibody:
   #86-2 or #176-1(10 ng to 1 µg/well)
   substrate concentration: 0.01%
   reaction time: 10 minutes
(2) the immobilized monoclonal antibody:
   #72-1(1 µg/well)
   the labeled monoclonal antibody:
   #86-2(1 to 3 ng/well)
   substrate concentration: 0.015%
   reaction time: 20 minutes
The results are shown in FIGS. 13 to 17.

As shown in FIGS. 13 to 17, the optimal concentration of the immobilized monoclonal antibody #72-1 was 1 µg/well (20 µg/ml) and that of the labeled monoclonal antibody, #86-2, was 100 ng/well(2 µg/ml) when the reaction time was 10 minutes, and 3 ng/well(60 ng/ml) when the reaction time was 20 minutes. Accordingly, the optimal concentration of the labeled monoclonal antibody may be set in accordance with reaction time since the optimal concentration depends on the reaction time.

In the following Examples, sandwich ELISA was employed, and the conditions were as follows:

the immobilized monoclonal antibody:
   #72-1(1 µg/well(20 µg/ml))
the labeled monoclonal antibody:
   #86-2(3 ng/well(60 µg/ml)) the reaction time with substrate: 20 minutes <7-4> Preparation of a Calibration Curve and Confirmation of Accuracy of the Present Assay
<7-4-1> Preparation of a Calibration Curve A calibration curve was prepared using the sandwich ELISA established in Example <7-3>. The purified human CETP prepared in <4-2> was used as a standard. As an immobilized monoclonal antibody, #72-1(1 µg/well), and as a labeled one, #86-2(3 ng/well) were also used. The result is shown in FIG. 18.

Figure 18:
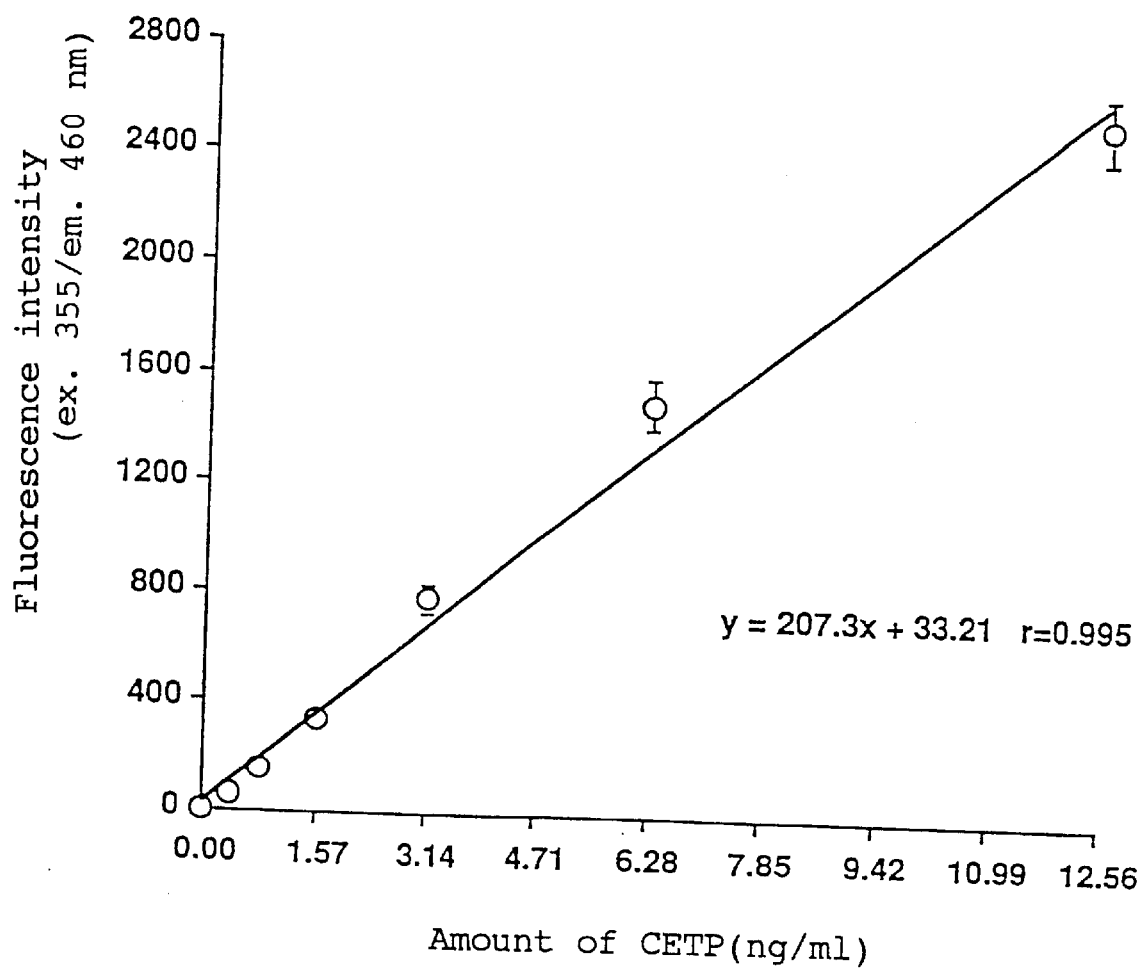
FIG. 18 shows a calibration curve of the purified human CETP standard preparations obtained from the quantification method of the present invention.

As shown in FIG. 18, the calibration curve was almost linear at the very low concentration range of between 0.4 to 1.25 ng/ml(correlation coefficient: r=0.995). The quantification limit(the detection limit) of a sandwich ELISA of the present invention was 0.4 ng/ml. Accordingly, it was demonstrated that, in comparison with the prior art, the sandwich ELISA of the present invention has excellent quantitative sensitivity, that is, excellent detection sensitivity.

<7-4-2> Calculation of Coefficient of Variation

In order to study the accuracy of the assay method of the present invention, the coefficient of variation(c.v.) in the same plate (among 48 wells in a 96 well plate) as well as in 6 different plates were calculated. The c.v. obtained in the same plate was 7.06%, and that obtained in different plates was 6.13%. Accordingly, it was demonstrated that the assay system by using sandwich ELISA of the present invention has high accuracy.

<7-5> Preliminary Experiment for the Establishment of the Human CETP Assay System
<7-5-1> Study of the Influence on the Quantitative(assay) Capability by the Components in Human Plasma In order to study the existence of the components in plasma which may affect the quantification capability of human CETP, the following tests were performed.

The purified human CETP prepared in Example <4-2> (0.735 µg/ml, or 1.469 µg/ml) was added to the healthy volunteers'plasma containing 0.56 µg/ml of CETP, which was prepared in the similar manner as in Example <2-1>. Then, the amount of CETP was determined by using the method established in the above-mentioned <7-3>.

When 0.735 µg/ml or 1.469 µg/ml of CETP was added, the total CETP amount of each sample before incubation was calculated as 1.294 µg/ml or 2.029 µg/ml, respectively. On the other hand, the total amounts of CETP recovered were 1.440 µg/ml and 2.189 µg/ml, and the recovery percentages were 111% and 108% respectively.

As a result, it was demonstrated that the human plasma did not contain any component which affects the quantification(assay) of CETP by the method of the present invention. Accordingly, it was shown that the amount of CETP in human plasma was accurately determined by using the method of the present invention.

<7-5-2> Influence of Lipoproteins in Human Plasma

In order to study the influence on quantitative sensitivity by substances such as lipoproteins except CETP for the human CETP quantification in human plasma, the human CETPs of different purity as assay samples were studied by using the assay system established in the above-mentioned <7-3>.

For the determination, the following samples were used;
(1) the plasma from which only hemocytes were removed by centrifugation in Example<2-1>,
(2) the plasma finally obtained in Example<2-1> in which lipoproteins were removed, (3) the purified CETP purified by the Phenyl Sepharose column in Example <2-2>, (4) the purified human CETP prepared in Example <4-2>

Figure 19:
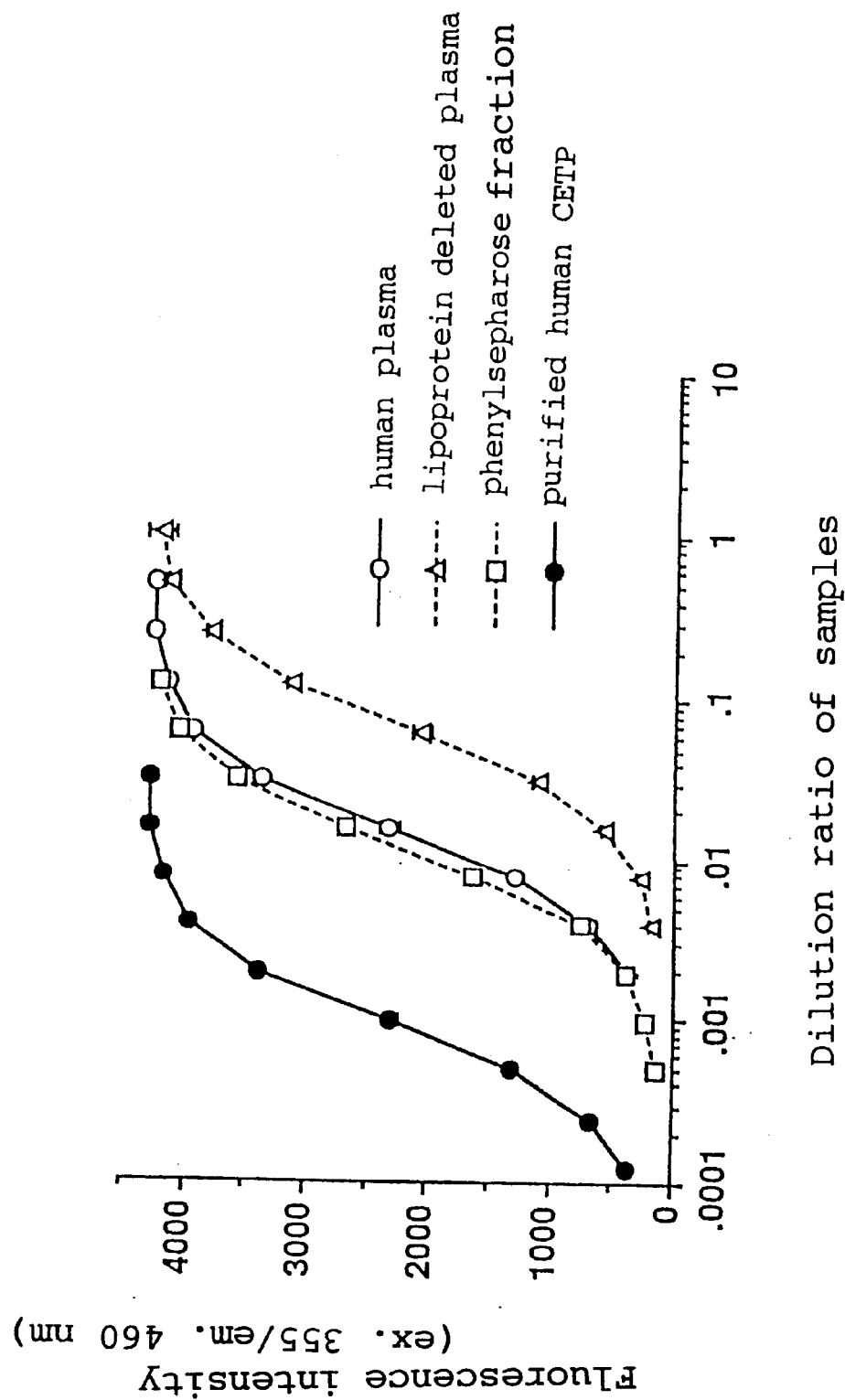
FIG. 19 shows a quantification of human plasma CETP with different purity by the quantification method of the present invention.

The result is shown in FIG. 19. Quantitative curves (Dilution curves) for the above samples (1), (2), and (3) obtained were respectively parallel with that of the purified human CETP(4).

As a result, it was demonstrated that the lipoproteins in human plasma did not affect the quantification of CETP by the method of the present invention. Accordingly, it was shown that the quantification method of the present invention may be applied to plasma irrespective of sample purity.

<7-5-3> Correlation of CETP Amount and CETP Activities

In order to investigate the precision of the quantification method of the present invention, a correlation between the determined CETP amount in the human plasma sample and the CETP activity of the plasma sample was investigated.

Figure 20:
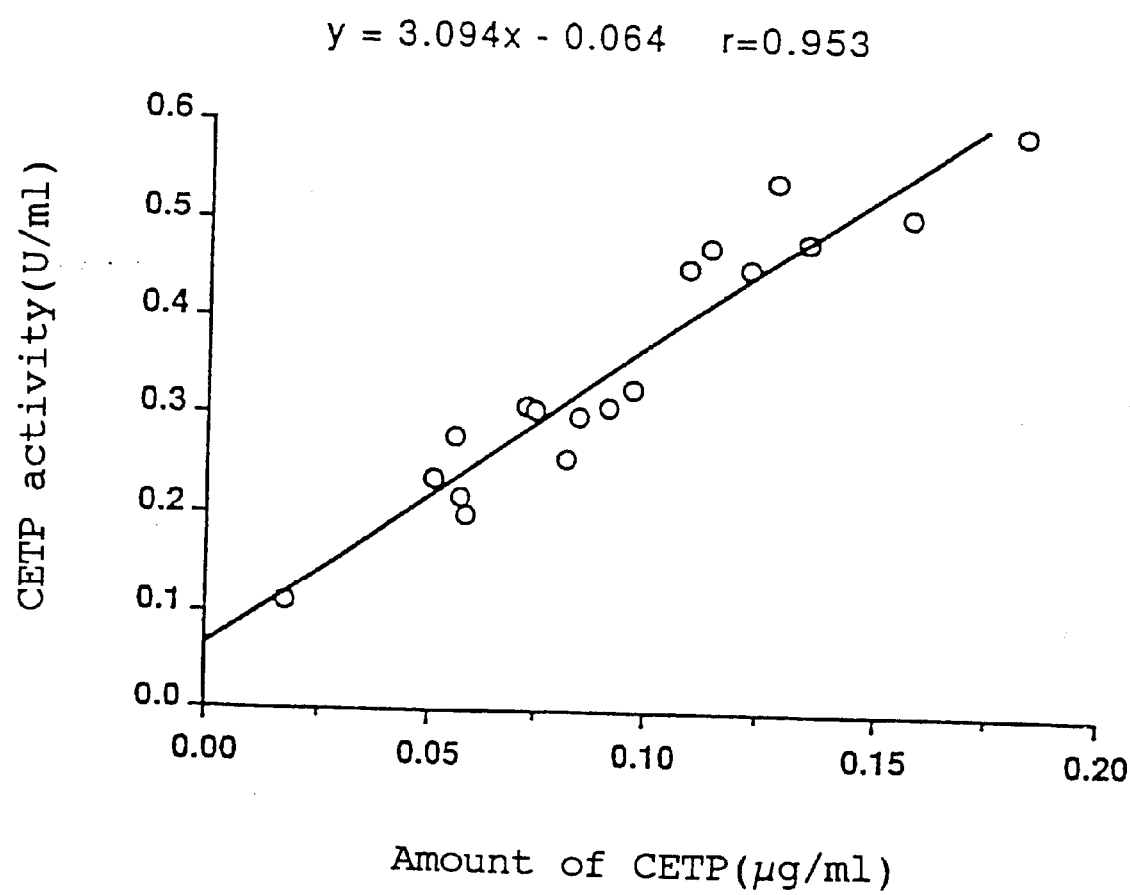
FIG. 20 shows a correlation between the activity of CETP and the amount of CETP in the samples determined by using the quantification method of the present invention.

Quantification of the CETP amount was demonstrated by using the lipoprotein-removed plasma obtained in Example <2-1> as an assay sample. CETP activity was measured by using the same plasma sample used in the above quantification, using the CETP assay system of Example 1. The result is shown in FIG. 20.

Since the correlation coefficient(r) obtained was 0.953, the amount of CETP determined by the method of the present invention and the CETP activities of the same sample show very high correlation. As a result, it was demonstrated that the assay system of the present invention has quite a high precision.

Example 8

Determination of Human CETP in Human Plasma

The amounts of CETP in the plasma from healthy volunteers or various patients were quantified by using the sandwich ELISA method established in Example <7-3>.

The CETP activity of the plasma was measured by using the donor lipoprotein([$^3$H]CE-HDL$_3$ which contains 6 μg of CE) prepared in a similar manner as in Example <1-1> and the acceptor lipoprotein (LDL which contains 600 μg of CE) prepared in a similar manner as in Example <1-2> with the CETP assay system established in Example <1-3>.

Figure 21:
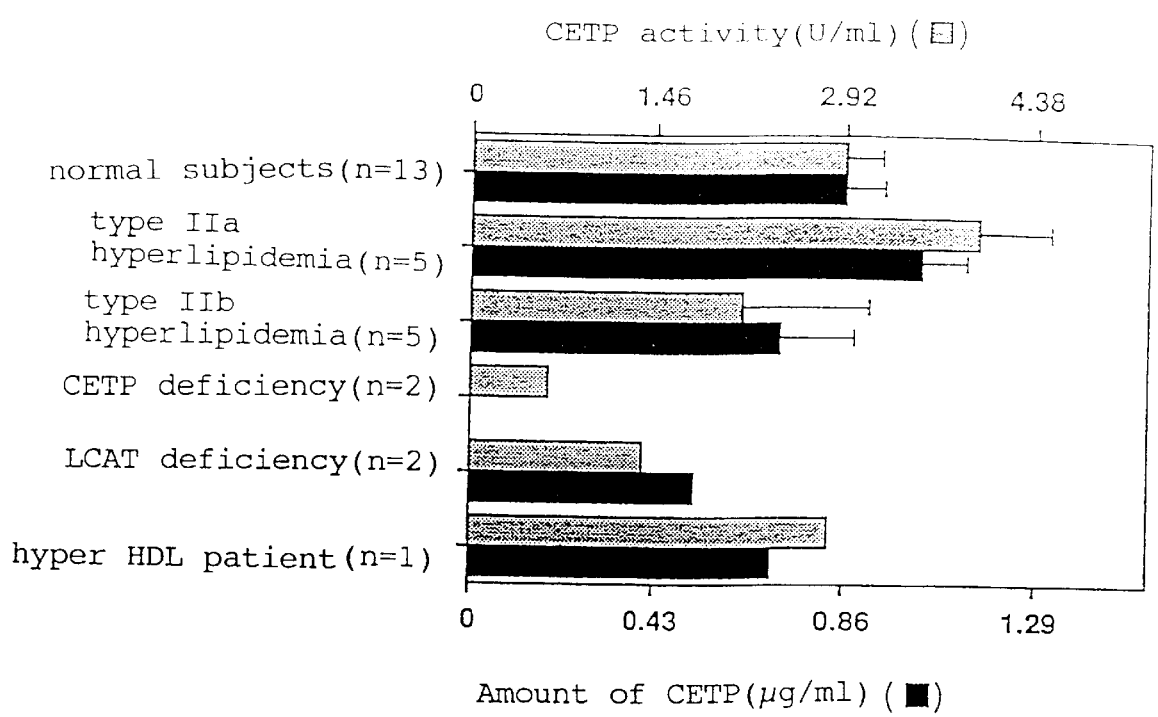
FIG. 21 shows the activity and the amount of plasma CETP from normal subjects or various patients determined by using the quantification method of the present invention.

The human plasma used in the present assay were from healthy volunteers(13), and patients of type IIa hyperlipidemia(5), type IIb hyperlipidemia(5), CETP deficiency(2), LCAT deficiency(2), and hyperaplhalipoproteinemia (hyper HDL patients) (1). Results are shown in FIG. 21.

Samples from the healthy volunteers and from various patients showed high correlations between the amount of CETP quantified and its CETP activity. As expected, CETP was not detected in the plasma from the patients with CETP deficiency. Furthermore, it was demonstrated that the assay method of the present invention may be applied not only to the plasma from healthy volunteers but also to those from patients with various diseases. (Example 9) Comparison with the conventional quantification method The following tests were performed to confirm the usefulness of the assay system of the present invention over the conventional method which employs sandwich ELISA to assay human CETP.

In the conventional method, prior to quantification, treatments by surface active agents (detergent) such as TRITON X-100 or heating have been performed to expose epitopes blocked by the protein-protein or proteinlipoprotein interaction. However, such treatments cause denaturation of the proteins such as CETP in the sample, and the protein loses its higher-order structure to become biologically inactive. Since CETP detected or determined by the conventional method is not intact CETP, but only denatured CETP, it is impossible to determine accurately the amount of CETP in the plasma.

Accordingly, the following were used as samples in the experiment.

Figure 22:
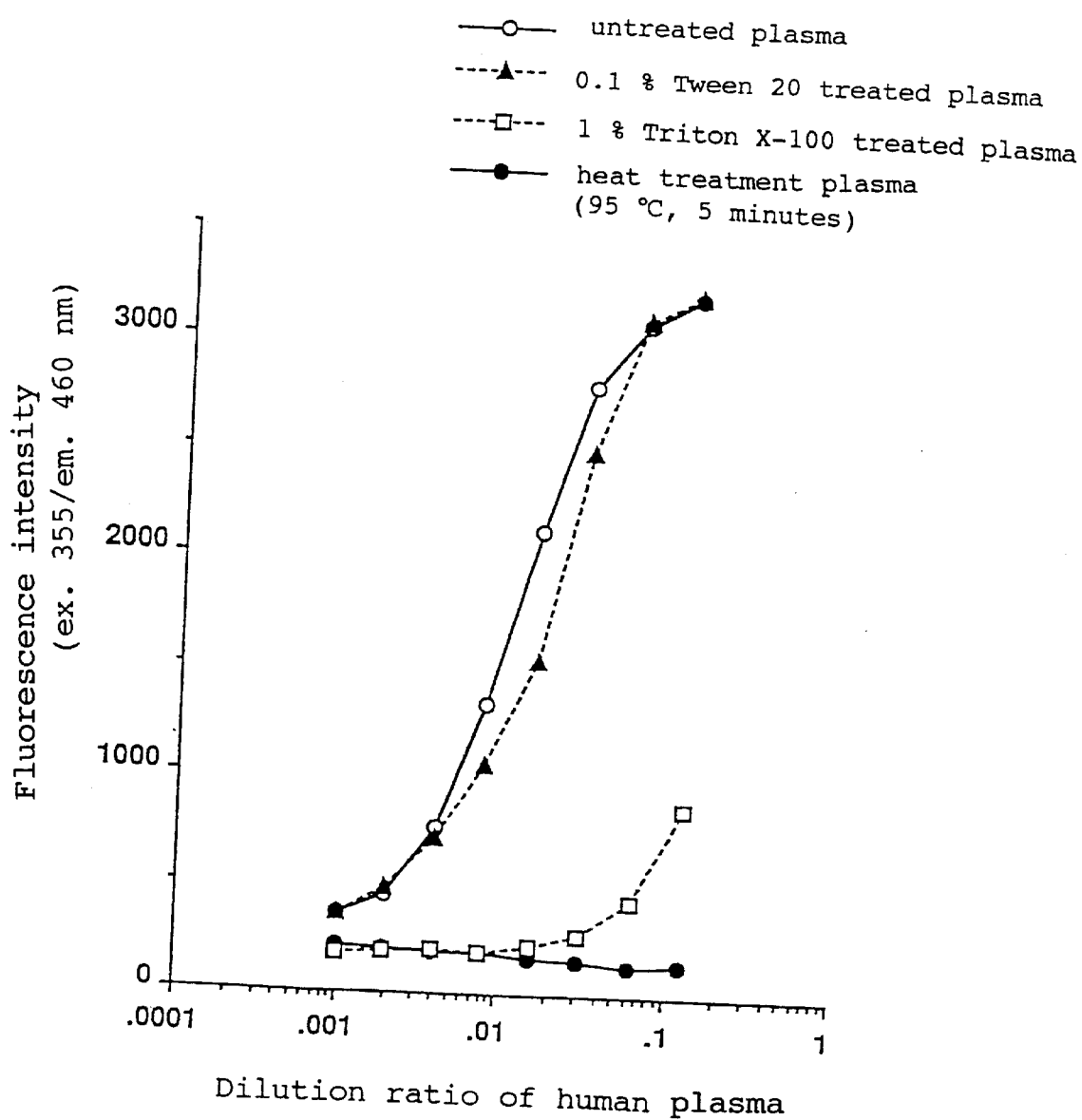
FIG. 22 shows the reactivity of the monoclonal antibodies, #72-1 or #86-2 to denatured human CETP, and the difference of the quantification methods between the present invention and the conventional ones.

(1) the plasma from healthy volunteers without lipoproteins prepared in the same manner as in Example <2-1> (a diluent of phosphate buffer with 10% Block Ace), (2) the plasma from healthy volunteers without lipoproteins, which was incubated with 0.1% TWEEN 20 (detergent), (3) the plasma from healthy volunteers without lipoproteins, which was heated at 95° C. for 5 minutes, (4) the plasma from healthy volunteers without lipoproteins, which was incubated with 1% TRITON X-100. The result is shown in FIG. 22.

CETP was not detected for plasmas treated with 1% TRITON X-1000 or by heat. In particular, absolutely no CETP was detected for the plasma treated by heat. Furthermore, quantification capability was decreased more than 30% in the plasma treated even with the low concentration of TWEEN 20. That is, it was confirmed that the precise quantification of intact CETP in the human plasma was enabled by using the assay method of the present invention, which has been impossible by the conventional determination(assay) method which requires the surface active agent treatment or heating, since the monoclonal antibody of the present invention has specific reactivity for intact CETP in the human plasma. Furthermore, it was also made clear that the known monoclonal antibodies for the human CETP react specifically to the denatured human CETP.

Example 10

Preparation of the Pharmaceutical Compositions and their CETP Inhibition Activity The purified monoclonal antibodies, #72-1, #86-2, and #176-1 as prepared in Example 3 were dissolved at the concentration of 50 to 150 μg/ml in 10 ml of distilled water for injections.

Anti-rabbit CETP monoclonal antibody was prepared in a similar manner as in Example 3 using the purified rabbit CETP prepared in Example <5-2-1> as the immunogen. That is, BALB/c mice(female, 4–5 weeks, Shizuoka Experimental Animal Center) weres immunized with the purified rabbit CETP to obtain two hybridomas, #2-64 and #9-1, which produced anti-rabbit monoclonal antibodies. Each hybridoma was transplanted into nude ICR mice(female, Charles River) to prepare anti-rabbit monoclonal antibodies from the ascites. The monoclonal antibodies #2-64 and #9-1 were obtained, and both are IgG1. The monoclonal antibody, #264, was dissolved in distilled water for injections at the concentration of 0.13 mg/ml. The monoclonal antibody #9-1 was at a concentration of 5.53 mg/ml. Thus prepared injections containing either #2-64 or #9-1 were administrated into a rabbit at a dose of 1.8 mg/kg of body weight intravenously. The time of the initial administration was set as 0, and the monoclonal antibodies were administrated at the same dose every 24 hr. The blood was sampled at 1, 2 and 24 hr from the initial administration to obtain plasma.

Figure 23:
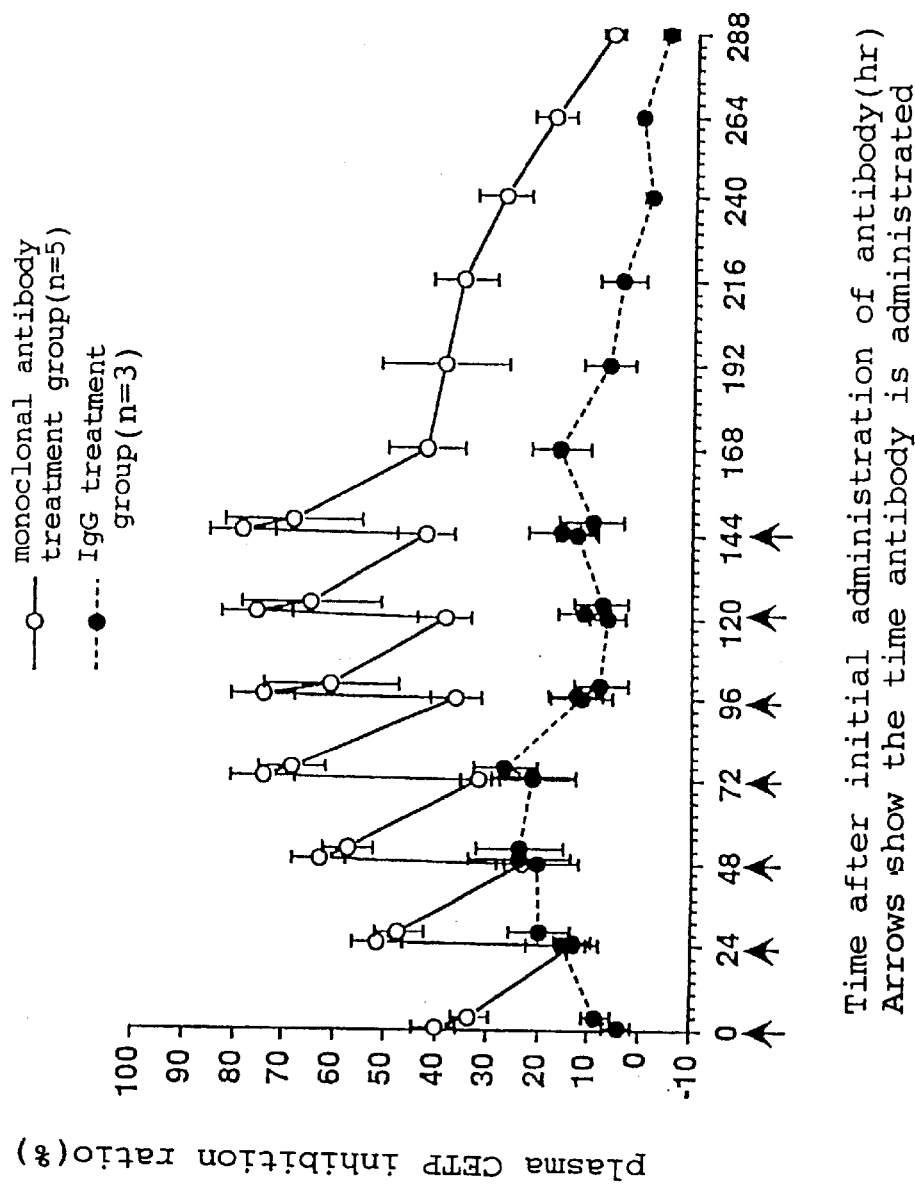
FIG. 23 shows the inhibitory effect of CETP activity by an anti-CETP monoclonal antibody in vivo test using rabbit.

The CETP activities in the plasma thus obtained were determined by using sandwich ELISA for the rabbit CETP quantification method established with the monoclonal antibodies #2-64 and #9-1 similarly as in Example 1. Results are shown in FIG. 23.

It was demonstrated that the monoclonal antibodies #2-64 and #9-1 significantly inhibit CETP in rabbit plasma.

(Example 11

Production of Transgenic Mice which Highly Express Human CETP

A plasmid containing cDNA encoding human CETP was obtained as follows. A cDNA fragment encoding human CETP was amplified by PCR with a 5'-stretch cDNA library of the human liver(Clonetech) as a template. The PCR products were separated by agarose gel electrophoresis by a known method. The cDNA fragment of interest was excised from the gel and the gel was dissolved by QIAEX (QUIAGEN). The fragment obtained was inserted into a pCR II vector(INVITROGEN). The pCR II vector was introduced into competent E. coli DH5 to obtain an amount of plasmid sufficient to perform DNA sequencing. After sequencing, the human CETP cDNA was confirmed.

The cDNA encoding the human CETP obtained above was treated with the DNA ligation kit(Takara), and inserted into a vector containing a human β-actin promoter(Mol. Cel. Immunol., 4:1961–1969(1984); ibid., 5:2720–2732(1985)) to obtain the plasmid pCETP-1. By electroporation, pCETP-1 was introduced into COS cells, and then after culturing the transformed COS cells, RNA was obtained according to a known method. RT-PCR was performed using the RNA to confirm the specific transcription of human CETP in the COS cells having introduced pCETP-1. Another transformant was produced similarly to the COS cells by using the expression vector pME 18S. The expression of human CETP in the transformant was assayed by using the sandwich ELISA established in Example 7. In order to produce transgenic mice, the plasmid pCETP-1 was linearized by treating with restriction enzyme.

Female ICR mice having a vaginal plug were employed as foster mother mice. These mice were obtained by mating female ICR white mice(Japan crea) with male ICR white mice with seminal duct ligation(Japan Crea). Black C57BL/6J mice(female, Japan Crea) were employed as mice to obtain embryos for human CETP gene introduction. These mice were obtained by mating black male C57BL/6J mice (Japan Crea) with black female C57BL/6J mice(Japan Crea), the females were given 5 units of PEAMEX and 5 units of PUBEROGEN(both from Sankyo) for superovulation. After mating, oviducts were excised from the female C57BL/6J mice to be treated with hyaluronidase to obtain embryos, which were then stored in a medium.

Introduction of a human CETP gene into the embryos was performed by using a manipulator under a microscope according to a known method. The embryo was retained by holding on a needle at 37° C. and the solution containing the linear gene of human CETP diluted in Tris-EDTA buffer was introduced into the male pronucleus of the embryo by using a DNA introducing needle.

After introducing the gene, only embryos keeping normal condition were selected. Then, fertilized eggs in which the human CETP gene has been integrated were inserted into oviducts within the ovary of the foster mother mice, i.e. the ICR white mice.

Tails of the progeny mice, called the hetero-mice from the foster mother mice, were cut off to investigate whether the human CETP gene was integrated into the mouse genomic gene. By using the PCR method, integration into the mouse genomic gene was confirmed, and the expression of the human CETP was also confirmed by using the sandwich ELISA established in Example 7.

Mating two hetero mice described above, transgenic mice which highly express human CETP were produced as homo mice.

Example 12

In Vivo CETP Inhibition by Anti-CETP Monoclonal Antibody

Two kinds of purified anti human CETP monoclonal antibodies, #72-1 and #86-2 prepared in Example 3, were dissolved in distilled water for injections at a concentration ratio of 29:1 to prepare injections.

The mixed injectable solution was administrated intraperitoreally to 3 of the female transgenic mice that were highly expressing human CETP produced in Example 11 at a dose of 100 mg/kg by single injection. These mice were fed freely a pellet type food for breeding for 4 months.

The time just before the antibody administration was set as 0, and opthalmo-blood was sampled at times 1, 3, 6, and 24 hr and the plasma was separated by centrifugation. The CETP activity in the plasma obtained(CETP inhibition activity by anti-human CETP antibody) was determined by measuring the amount of CE(choresterol ester) transported from HDL to LDL by using the CETP activity quantification system established in Example 1.

Figure 24:
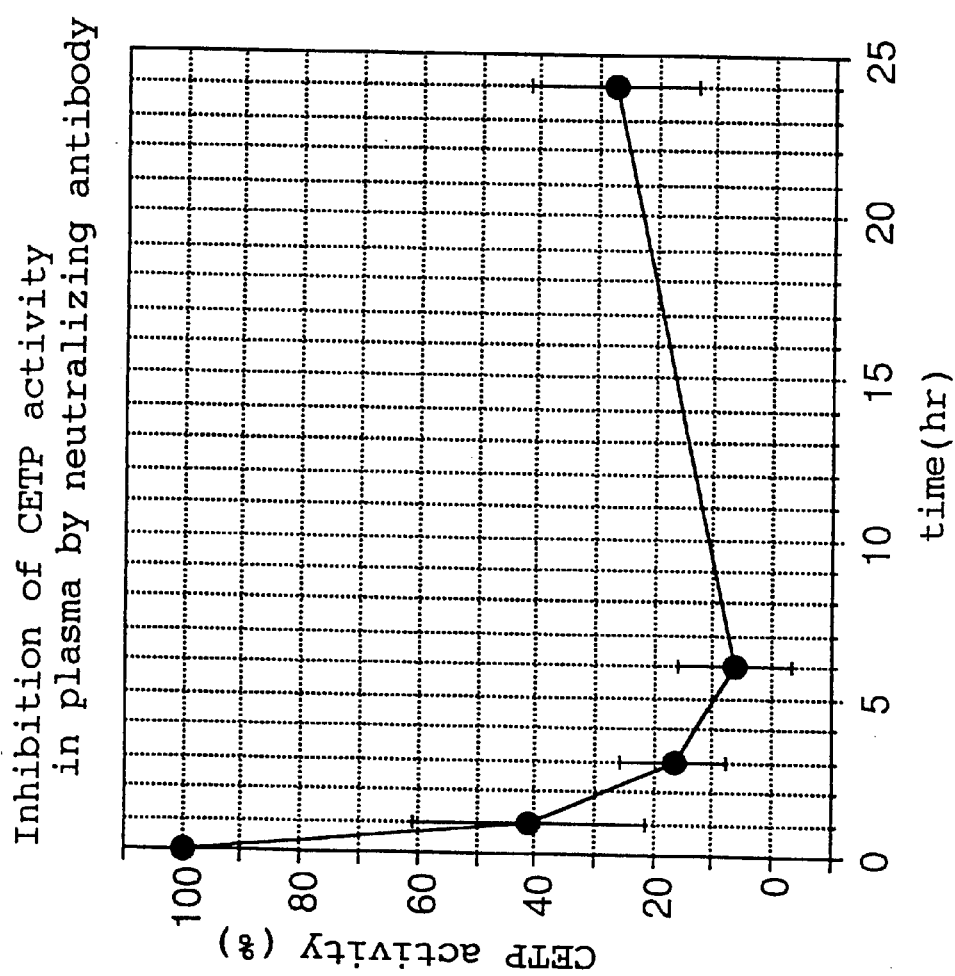
FIG. 24 shows the inhibitory effect of CETP activity by an anti-human CETP monoclonal antibody in vivo test using transgenic mice which highly express human CETP.

The result is shown in FIG. 24.

It was confirmed that the monoclonal antibody of the present invention completely inhibits the human CETP activity in vivo. Furthermore, such inhibition effect for the human CETP activity in vivo was first clarified by the present invention.

Example 13

Prevention of Arteriosclerosis by Anti-CETP Monoclonal Antibody

Two kinds of purified anti-human CETP monoclonal antibodies, #72-1 and #86-2 prepared in Example 3, were dissolved in distilled water for injections at a concentration ratio of 29:1 to prepare injections.

The mixed injectable solution was administrated intraperitoreally to 3 of the female transgenic mice highly expressing human CETP that were produced in Example 11 at a dose of 75 mg/kg per injection per day for 4 days. These mice were freely fed a pellet type food for breeding for 6 weeks. PBS(Phosphate buffered saline) was administrated to other mice as a control.

Figure 25:
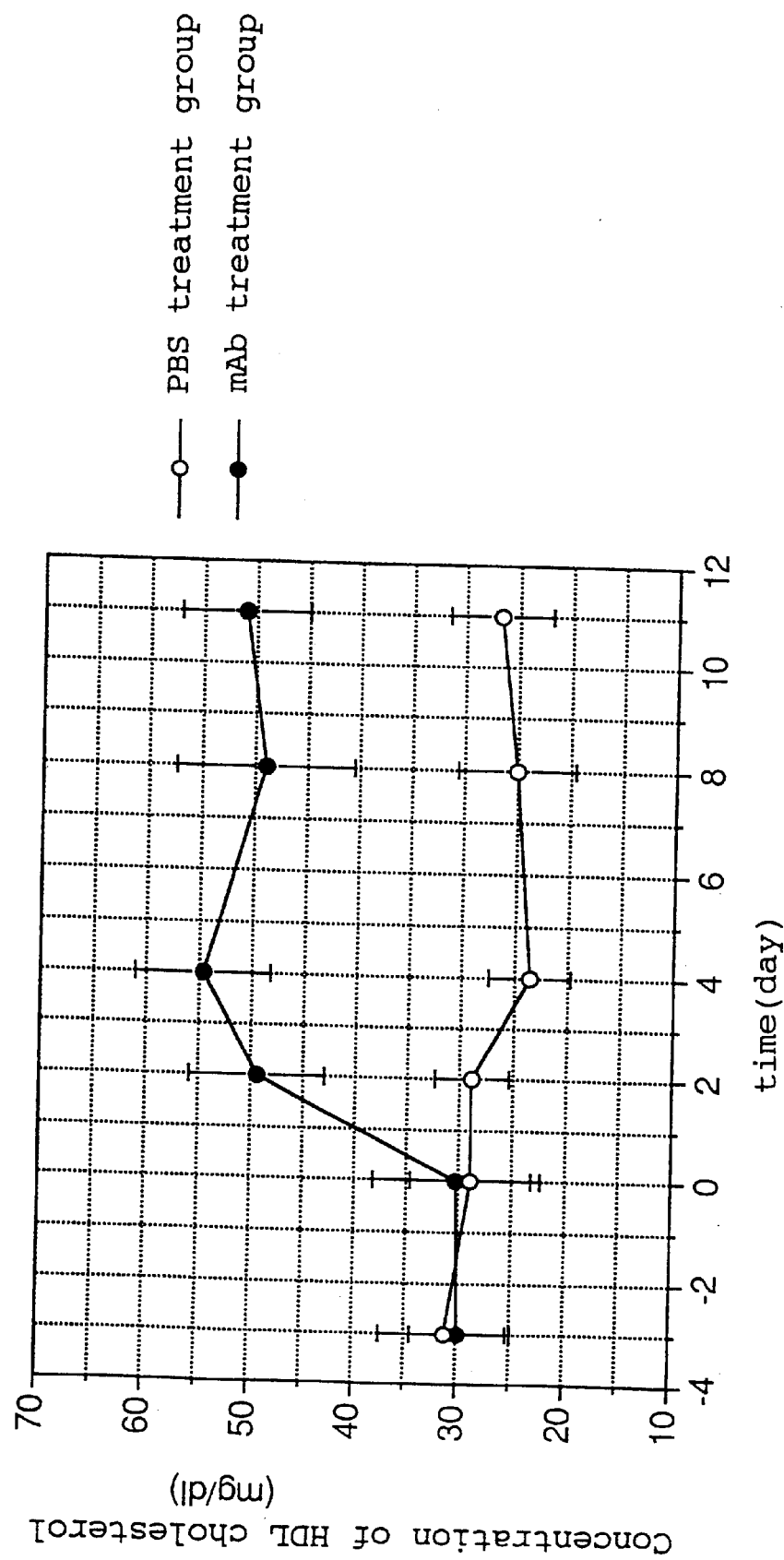
FIG. 25 shows the effect on the HDL choresterol level in blood by an anti-human CETP antibody in vivo test.

The time just before the antibody administration was set as 0. Opthalmo-blood was sampled at days 2, 4, 8, and 11 and the plasma was separated by centrifugation. The amounts of HDL cholesterol in the plasma obtained were determined using the lipoprotein determination kit(Liquitec TC1/TC2, Boehringer Mannheim). For the fractionation of HDL, HDL cholesterol separation reagent(Boehringer Mannheim) was employed. The result is shown in FIG. 25.

It was demonstrated that the HDL cholesterol level in blood rose significantly when the anti-human CETP monoclonal antibody of the present invention was administered in vivo. HDL is considered to be an important lipoprotein having anti-arteriosclerosis effect. In fact, it was shown that the development of atherosclerosis lesions was prevented or reduced by the increase of HDL in blood(J. Clin. Invest., 85:1234–1241(1990)).

The observation that the administration of the anti-human CETP antibody in vivo increases the HDL cholesterol level in blood was clarified first by the present invention. Accordingly, the result of the above-mentioned test reveals that the monoclonal antibody of the present invention is very useful for prevention and/or treatment of arteriosclerosis.

From the high inhibitory activity of human CETP by the monoclonal antibody of the present invention shown by Example 5-1 and from the results obtained in Examples 10 to 13, it was shown clearly that the monoclonal antibody of the present invention is useful in treating and preventing disorders caused by the abnormal kinetics of CETP in the body such as hyperlipidemia or arteriosclerosis.

INDUSTRIAL UTILITY

Since the anti-human CETP monoclonal antibody of the present invention has a higher binding specificity(CETP inhibition activity) to human CETP, particularly to intact CETP in the human body fluid, intact CETP in human body fluid such as plasma can be determined conveniently and with high sensitivity. Such determination(assay) method has not been established before.

Particularly, based on the above-mentioned characteristics of any of three anti-human CETP monoclonal antibodies of the present invention, the intact CETP in a human body can be quantified more conveniently and sensitively when any combination of the two monoclonal antibodies described above are employed in a sandwich ELISA.

In the quantification method employing the monoclonal antibody of the present invention, the amount of CETP in a bodily fluid such as plasma is quantified conveniently with high sensitivity without any pretreatment such as by a surface active agent or heating.

Since the anti-human CETP monoclonal antibody of the present invention has excellent CETP inhibition activity, it is useful as a pharmaceutical for prevention and/or treatment for various diseases such as arteriosclerosis, hyperlipidemia, and hyperalphalipoproteinemia caused by abnormal kinetics of CETP.

What is claimed is:

1. An anti-human CETP monoclonal antibody or a F(ab')$_2$ or Fab' fragment from said monoclonal antibody,
    wherein said monoclonal antibody inhibits cholesterol ester transfer activity of human CETP and does not inhibit cholesterol ester transfer activity of rabbit CETP at a concentration of 3 µg/ml or below, and
    wherein said monoclonal antibody provides a lower detection limit in an immunoassay of human CETP in non-pretreated human plasma than in human plasma pretreated by detergent or heating.

2. A recombinant chimeric monoclonal antibody or a F(ab')$_2$ or Fab' fragment from said monoclonal antibody,
    wherein said monoclonal antibody comprises a variable region from the monoclonal antibody of claim 1 and a constant region from a human immunoglobulin.

3. A recombinant humanized monoclonal antibody or a F(ab')$_2$ or Fab' fragment from said monoclonal antibody,
    wherein said monoclonal antibody comprises a part of or the whole of the complementarity determining regions of the hypervariable region from the monoclonal antibody of claim 1, framework regions of the hypervariable region from a human immunoglobulin and a constant region from a human immunoglobulin.

4. An immobilized monoclonal antibody or immobilized antibody fragment which is prepared by immobilizing the monoclonal antibody or F(ab')$_2$ or Fab' fragment of claim 1 on an insoluble carrier.

5. The immobilized monoclonal antibody or immobilized F(ab')$_2$ or Fab' fragment of claim 4 wherein said insoluble carrier is selected from the group consisting of a plate, a test tube, a tube, beads, a ball, a filter and a membrane.

6. The immobilized monoclonal antibody or immobilized F(ab')$_2$ or Fab' fragment of claim 4 wherein said insoluble carrier is one used for affinity purification.

7. A labeled monoclonal antibody or labeled antibody fragment which is prepared by labeling the monoclonal antibody or F(ab')$_2$ or Fab' fragment of claim 1 with a labeling substance that provides a detectable signal independently or by reaction with another substance.

8. The labeled monoclonal antibody or labeled F(ab')$_2$ or Fab' fragment of claim 7 wherein said labeling substance is selected from the group consisting of an enzyme, a fluorescent material, a chemiluminescent material, biotin, avidin and a radioisotope.

9. A kit for immunoassay to detect human CETP comprising the monoclonal antibody or F(ab')$_2$ or Fab' fragment of claim 1.

10. A kit for immunoassay to detect human CETP comprising the labeled monoclonal antibody or labeled F(ab')$_2$ or Fab' of claim 7.

11. A kit for separation or purification of human CETP comprising the immobilized monoclonal antibody or immobilized F(ab')$_2$ or Fab' fragment of claim 6.

12. A composition comprising the monoclonal antibody or F(ab')$_2$ or Fab' fragment of claim 1; and a pharmaceutically acceptable carrier.

13. A composition comprising the chimeric monoclonal antibody or F(ab')$_2$ or Fab' fragment of claim 2; and a pharmaceutically acceptable carrier.

14. A composition comprising the humanized monoclonal antibody or F(ab')$_2$ or Fab' fragment of claim 3; and a pharmaceutically acceptable carrier.

* * * * *